United States Patent [19]
Seeman et al.

[11] Patent Number: 6,072,044
[45] Date of Patent: Jun. 6, 2000

[54] NANOCONSTRUCTIONS OF GEOMETRICAL OBJECTS AND LATTICES FROM ANTIPARALLEL NUCLEIC ACID DOUBLE CROSSOVER MOLECULES

[75] Inventors: Nadrian Seeman; Xiaojun Li; Xiaoping Yang; Jing Qi, all of New York, N.Y.

[73] Assignee: New York University, New York, N.Y.

[21] Appl. No.: 08/827,974

[22] Filed: Apr. 25, 1997

Related U.S. Application Data

[60] Provisional application No. 60/016,233, Apr. 26, 1996.

[51] Int. Cl.[7] .......................... C07H 19/00; C07H 21/02; C07H 21/00; C12Q 1/68
[52] U.S. Cl. ...................... 536/22.1; 536/23.1; 536/25.3; 435/6
[58] Field of Search ................................. 536/22.1, 23.1, 536/25.3; 435/6

[56] References Cited

U.S. PATENT DOCUMENTS

| | | | |
|---|---|---|---|
| 5,278,051 | 1/1994 | Seeman et al. | 435/91.52 |
| 5,386,020 | 1/1995 | Seeman et al. | 536/23.1 |
| 5,468,851 | 11/1995 | Seeman et al. | 536/22.1 |

FOREIGN PATENT DOCUMENTS

WO85/00813  2/1985  WIPO.

OTHER PUBLICATIONS

Seeman, Nadrian C., "Construction of three–dimensional stick figures from branched DNA.", DNA and Cell Biology, vol. 10, No. 7, pp. 475–486 (1991).

Seeman, Nadrian C. et al., "Construction of a DNA–truncated octahedron.", J. Am. Chem. Soc., vol. 116, pp. 1661–1669 (1994).

Zhang, Siwei et al., "Symmetric holliday junction crossover isomers.", J. Mol. Biol., vol. 238, pp. 658–668 (1994).

Fu, Tsu–Ju et al., "DNa double–crossover molecules.", Biochemistry, vol. 32, pp. 3211–3220 (1993).

Zhang, Siwei et al., "Symmetric immobile DNA branched junctions.", Biochemistry, vol. 32, pp. 8062–8067 (1993).

Fu, Tsu–Ju et al., "Holliday junction crossover topology.", J. Mol. Biol., vol. 236, pp. 91–105 (1994).

Fu, Tsu–Ju et al., "Cleavage of double–crossover molecules by T4 endonuclease VII.", Biochemistry, vol. 33, pp. 3896–3905 (1994).

Wang, Hui et al., "Structural domains of DNA mesojunctions." Biochemistry, vol. 34, pp. 920–929 (1995).

Seeman, Nadrian C. et al., "Chemical synthesis of nanostructures.", Mat. Res. Soc. Symp. Proc., vol. 330, pp. 45–56 (1994).

Liu, Bing et al., "Bulged three–arm DNA branched junctions as components for nanoconstruction.", Nanobiology, vol. 3, pp. 177–188 (1994).

*Primary Examiner*—Jezia Riley
*Attorney, Agent, or Firm*—Browdy and Neimark

[57] ABSTRACT

Two and three dimensional polynucleic acid structures, such as periodic lattices, may be constructed from an ordered array of antiparallel double crossover molecules assembled from single stranded oligonucleotides or polynucleotides. These antiparallel double crossover molecules have the structural rigidity necessary to serve as building block components for two and three dimensional structures having the high translational symmetry associated with crystals.

19 Claims, 21 Drawing Sheets

DAE

DAO

LIGATED DAE

LIGATED DAO

TGATCTCC  TGTGC  CAGGG  ACAACTTGCGGC
STRAND 2a

FIG. 12
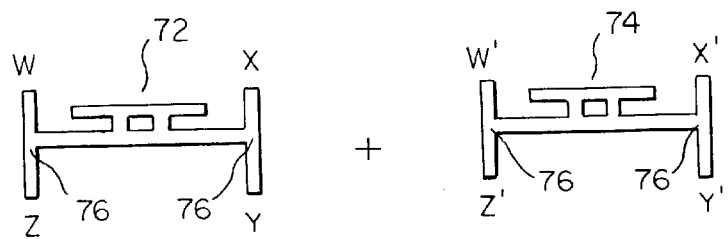
↓ RESTRICT TO EXPOSE ENDS
 LIGATE
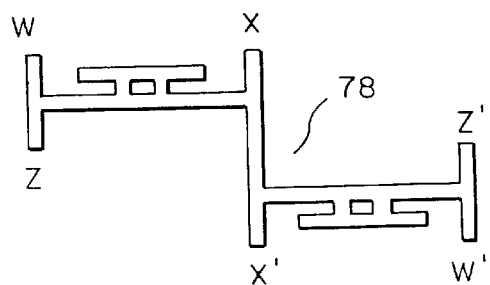
↓ RESTRICT TO EXPOSE ENDS
 LIGATE
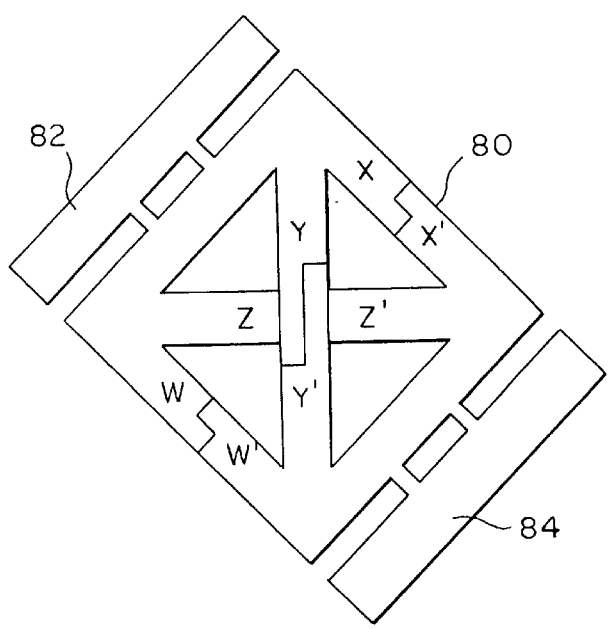

FIG. 13
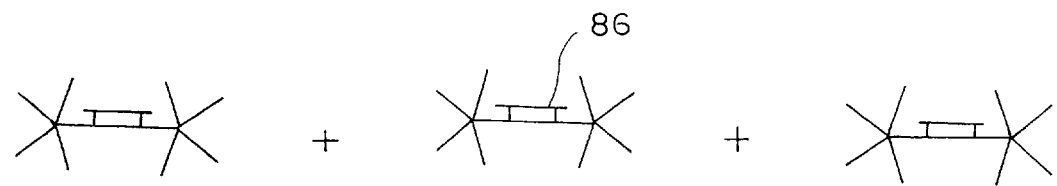
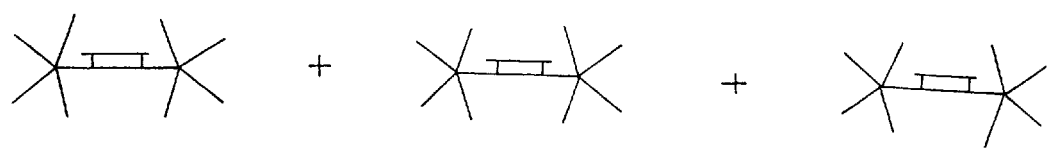
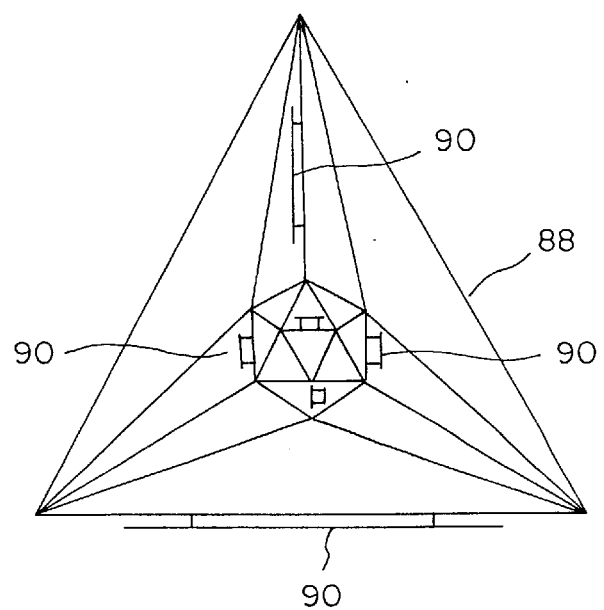

RESTRICT TO EXPOSE ENDS
LIGATE

| LANES     | 1 | 2 | 3 | 4 | 5 | 6 | 7 | 8 | 9 | 10 | 11 |
|-----------|---|---|---|---|---|---|---|---|---|----|----|
| STRANDS 1 | + | − | − | − | + | − | − | − | − | −  | −  |
| 1a        | − | + | − | − | − | + | + | + | + | −  | +  |
| 2         | − | − | − | − | − | − | − | + | − | −  | −  |
| 2a        | − | − | + | − | + | + | + | − | + | +  | −  |
| 3         | − | − | − | + | + | + | − | + | − | +  | +  |
| 3a        | − | − | − | − | − | − | + | − | − | −  | −  |
| 3b        | − | − | − | − | − | − | + | − | − | −  | −  |

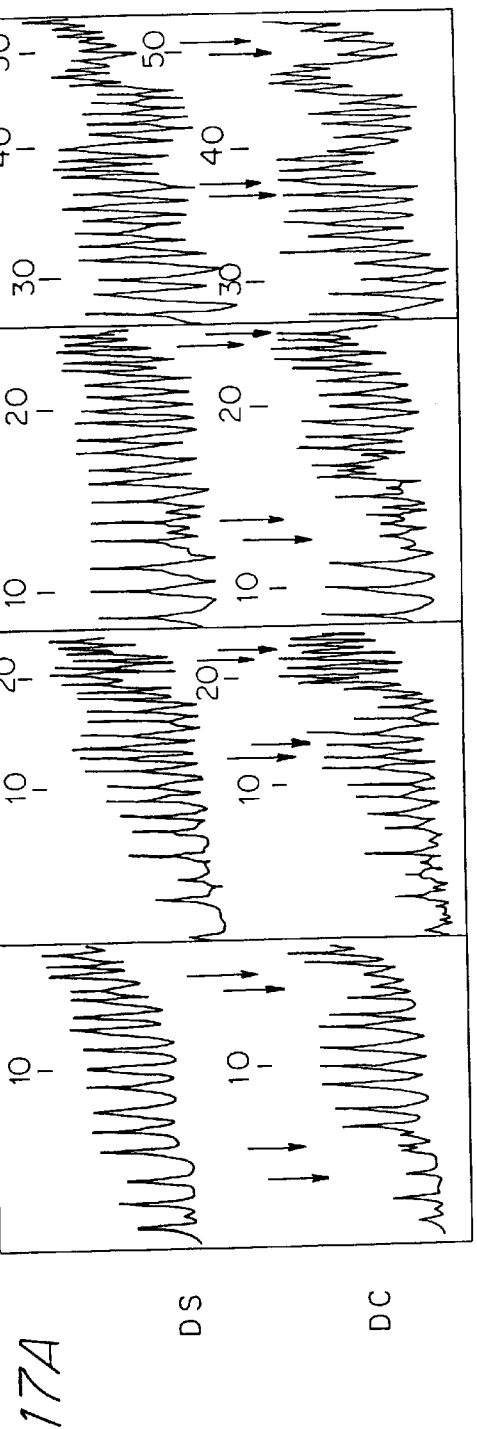
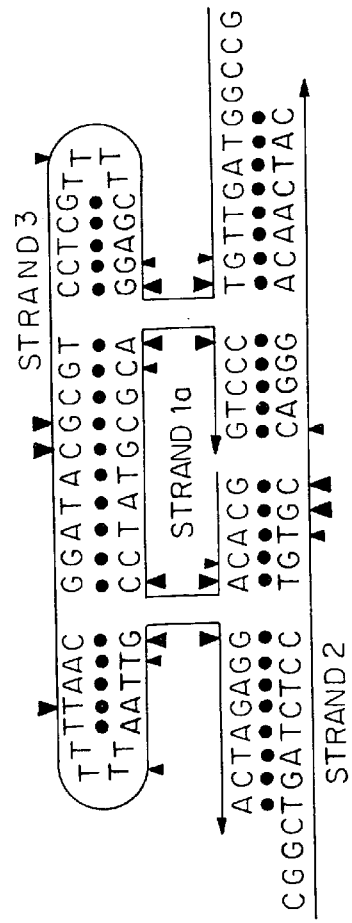
FIG. 17A
FIG. 17B

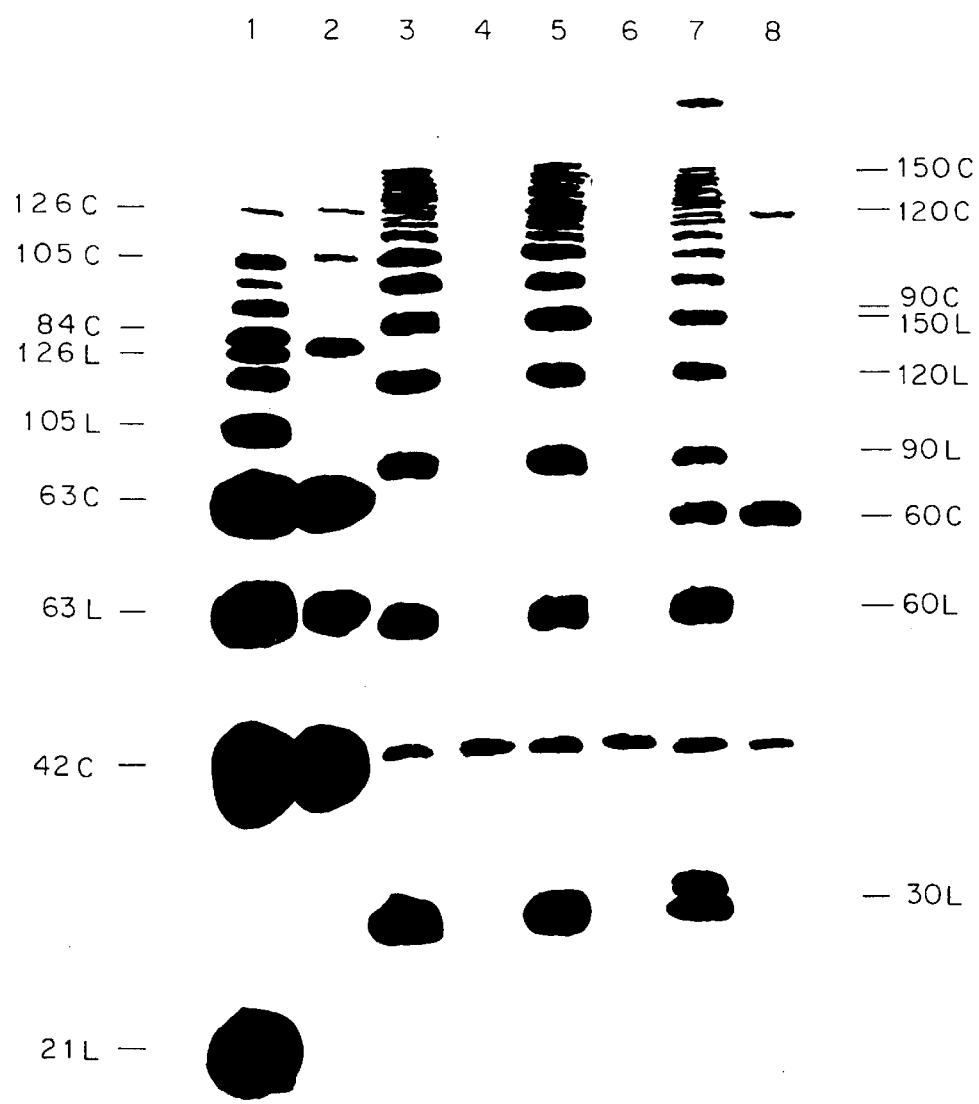

| LANES | 1 | 2 | 3 | 4 | 5 | 6 | 7 | 8 |
|---|---|---|---|---|---|---|---|---|
| | JY21 | | DX + JUNCTION | | | | DX WITH NICKS | |
| LIGASE | + | + | + | + | + | + | + | + |
| HhaI | − | − | − | − | + | + | − | − |
| ExoI-III | − | + | − | + | − | + | − | + | ial
NANOCONSTRUCTIONS OF GEOMETRICAL OBJECTS AND LATTICES FROM ANTIPARALLEL NUCLEIC ACID DOUBLE CROSSOVER MOLECULES

CROSS-REFERENCE TO RELATED APPLICATION

The present application claims priority under 35 USC §119(e) from U.S. Provisional application No. 60/016,233 filed Apr. 26, 1996 abandoned, the entire contents of which are hereby incorporated by reference.

GOVERNMENT LICENSE RIGHTS

The experiments performed in this application were supported in part by the Office of Naval Research, grant number N00014-89-J-3078, and the National Institutes of Health, Grant No. GM-29554. The U.S. Government has a paid-up license in this invention and the right in limited circumstances to require the patent owner to license others on reasonable terms as provided for by the terms of Grant No. N00014-89-J-3078 awarded by the Office of Naval Research, and Grant No. GM-29554 awarded by the National Institutes of Health.

BACKGROUND OF THE INVENTION

1. Field of the Invention

The present invention relates to nucleic acid structures and to symmetrical and asymmetrical two dimensional and three dimensional polynucleic acid structures with symmetrical intermolecular contacts formed from joining antiparallel double crossover molecules. In addition, the present invention relates to the method for producing such polynucleic acid structures.

2. Description of the Related Art

A key aim of biotechnology and nanotechnology (Feynman et al., *Miniaturization*, 282–296, 1961 and Drexler, *Proc. Nat. Acad. Sci.* (*USA*) 78: 5275–5278, 1981) is a rational approach to the construction of new biomaterials, including individual geometrical objects and nanomechanical devices, and extended constructions, particularly periodic matter with control of the molecule architecture such that it would permit the fabrication of intricate arrangements of atoms to serve many practical purposes (Robinson et al. *Prot. Eng.* 1: 295–300, 1987; Seeman, *DNA & Cell Biol.* 10: 475–486, 1991; Seeman, *Nanotechnol.* 2: 149–159, 1991). The informational macromolecules of biological systems, proteins and nucleic acids, are believed to have the potential to serve as building blocks for these constructions, because they are used for similar purposes in the cell. For instance, nanometer-scale circuitry and robotics could accomplish many tasks that are impossible today. One can envision improvements in the storage and retrieval of information, directed attacks on the molecular basis of medical problems, and the assembly of very smart materials as possible end products of the ability to control the structure of matter on the nanometer scale.

The laboratory of the present inventors has been engaged in the nanoscale construction of stick figures, using branched DNA molecules as building blocks. The edges of these figures consist of double helical DNA, and the vertices correspond to the branch points of stable DNA branched junctions (Seeman, *J. Theor. Biol.* 99: 237–247, 1982; Seeman, J. Biomol. Str. & Dyns. 3: 11–34, 1985). The molecules can be assembled in solution or on solid supports. The molecules reported previously contain helix axes that have the connectivities of a quadrilateral (Chen et al., *J. Am. Chem. Soc.* 111: 6402–6407, 1989; U.S. Pat. Nos. 5,278,051 and 5,468,851) a Platonic polyhedron, a cube (Chen et al., *Nature* (London) 350: 631–633, 1991; U.S. Pat. No. 5,386, 020) an Archimedean polyhedron, i.e., a truncated octahedron (Zhang et al., *J. Am. Chem. Soc.* 116: 1661–1669, 1994). If the edges of DNA polyhedra are designed to contain an integral number of double helical turns, every face corresponds to a cyclic strand of DNA, which is linked to each of its neighbors. Thus, the cube is a hexacatenane, and the truncated octahedron is a 14-catenane of DNA; the extent of linking between faces is equal to the number of turns in the edge where they meet. Both the polyhedra contain two turns per edge, so each of their cyclic strands is doubly linked to each of its neighbors.

The construction of discrete closed structural entities, such as polyhedra, can be controlled readily, because the sequence symmetry of the molecules can be limited by the molecular design. Thus, the ligation of identical DNA sticky end pairs (to yield an edge) can be separated from each other in time by protection techniques (Zhang et al., *J. Am. Chem. Soc.* 114, 2656–2663, 1992 and U.S. Pat. Nos. 5,278,051 and 5,468,851; the use of sticky ends with unique sequences also provides control over the assembly of finite objects (Chen et al., 1989, supra). This situation does not apply to the construction of periodic matter (crystals), where translational symmetry is an inherent characteristic of the system, because the contacts between all unit cells are identical. It is possible to envision deprotection schemes to unmask, successively, individual polyhedra or polyhedral clusters containing the same sticky ends by means of different restriction enzymes (Seeman et al., *Biomolecular Materials: Materials Res. Soc. Symp. Proc.* 242: 123–134, 1993). Likewise, one can imagine the construction of 'pseudocrystals', having the same backbone structure and topology in each unit cell, but differing in sequence at key sites. Such schemes may be applicable to DNA computing (Adleman *Science* 266: 1021–1024, 1994), but they are both cumbersome and expensive and they do not offer a practical route to the assembly of large repetitive constructs, even if one pictures hierarchical assembly of subsections of the target crystal.

There are at least three key elements necessary for the control of three-dimensional structure in molecular construction that involves the high symmetry associated with crystals: (1) the predictable specificity of intermolecular interactions between components; (2) the structural predictability of intermolecular products; and (3) the structural rigidity of the components (Liu et al., *Nanobiol.* 3: 177–188, 1994). DNA branched junctions are excellent building blocks from the standpoint of the first two requirements, which are also needed for the construction of individual objects, because, (1) ligation directed by Watson-Crick base pairing between sticky ended molecules has been used successfully to direct intermolecular specificity since the early 1970's (Cohen et al., *Proc. Natl. Acad. Sci.* (*USA*) 70: 3240–3244, 1973); and (2) the ligated product is double helical B-DNA, whose local structural parameters are well-known (Arnott et al., *J. Mol. Biol.* 81: 93–105, 1973).

The key problem in working with branched DNA as a construction medium is that branched junctions have been shown to be extremely flexible molecules (Ma et al., *Nucl. Acids. Res.* 14: 9745–9753, 1986; Petrillo et al., *Biopolymers* 27: 1337–1352, 1988). The ligation of 3-arm and 4-arm DNA branched junctions leads to many different cyclic products, suggesting that the angles between the arms of the junctions vary on the ligation time-scale; these angles are analogous to valence angles around individual atoms. Likewise, a 5-arm DNA branched junction has been shown to have no well-defined structure, and a 6-arm DNA branched junction has only a single preferred stacking domain (Wang et al., *Biochem.* 30: 5667–5674). Leontis and his colleagues have shown that a three-arm branched junction containing a loop of two deoxythymidine nucleotides has a preferred stacking direction (Leontis et al., *Nucl. Acids Res.* 19: 759–766, 1991) and ligation along this direction shows a lower propensity to cyclization (21.3%) than other directions (Liu et al., 1994, supra), but it is not possible to treat the stacking domain in the Leontisian junction as a rigid component (Qi et al. 1996).

To overcome the problem of branched DNA being extremely flexible and therefore unsuitable from the standpoint of structural rigidity of the components as the third key element, DNA structures that fail to cyclize significantly in the course of ligation reactions (a measure of the rigidity of the DNA) were sought by the present inventors. DNA double crossover molecules, which are model systems for structures proposed to be involved in genetic recombination initiated by double strand breaks (Sun et al., *Cell* 64: 1155–1161, 1991; Thaler et al., *Ann. Rev. Genet.* 22: 169–197, 1988), as well as meiotic recombination (Schwacha et al., *Cell* 83: 783–791, 1995), were explored with respect to the structural features of these molecules, and the inventors' laboratory has shown that there are five different isomers of double crossover molecules (Fu et al., *Biochem.* 32: 3211–3220, 1993). Double crossover molecules were used in the laboratory of the present inventor to establish the sign of the crossover node in the Holliday junction (Fu et al., *J. Mol. Biol.* 236: 91–105, 1994), to construct symmetric immobile branched junctions (Zhang et al., *J. Mol. Biol.* 238: 658–668, 1994), and to examine the effect of domain orientation on cleavage by the Holliday junction resolvase, endonuclease VII (Fu et al., *Biochemistry* 33: 3896–3905, 1994). The helical domains were found to be parallel in three of the five isomers, and antiparallel in the other two. Those with parallel domains are not as well-behaved as those with antiparallel domains (Fu et al., 1993, supra).

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention is based on the quite surprising discovery that antiparallel nucleic acid double crossover molecules were stiffer than branched junctions with the same sequence and at least as stiff as linear duplex DNA of the same sequence, making them surprisingly amenable to serving as building block components for symmetrical and asymmetrical polynucleic acid structures whose components associate with symmetrical contacts from unit cell to unit cell. These antiparallel nucleic acid double crossover molecules were found to be at least as stiff as linear duplex DNA as determined by ligating these molecules to form multimers and determining the amount, if any, of cyclized multimers formed.

The polynucleic acid molecules and structures of the present invention are assembled from antiparallel nucleic acid double crossover molecules according to the method of the present invention.

It is an object of the present invention to overcome the deficiencies of the prior art such as providing structural rigidity to branched nucleic acid molecules capable of joining together to form a polynucleic acid structure where components initially have identical (symmetrical) contacts.

Another object of the present invention is to provide a polynucleic acid structure which is composed of three interconnected antiparallel nucleic acid double crossover molecules.

A further object of the present invention is to provide a two dimensional or three dimensional symmetrical and asymmetrical structures composed of an arrangement of polynucleic acids formed from interconnected antiparallel nucleic acid double crossover molecules.

Still another object of the present invention is to provide a two dimensional polynucleic acid structure having a hexagonally symmetric periodic lattice formed from interconnecting triangles of antiparallel nucleic acid double crossover molecules.

Yet another object of the present invention is to provide a method of forming a two dimensional or three dimensional polynucleic acid structure composed of interconnected antiparallel nucleic acid double crossover molecules.

Figures 4A, 4B:
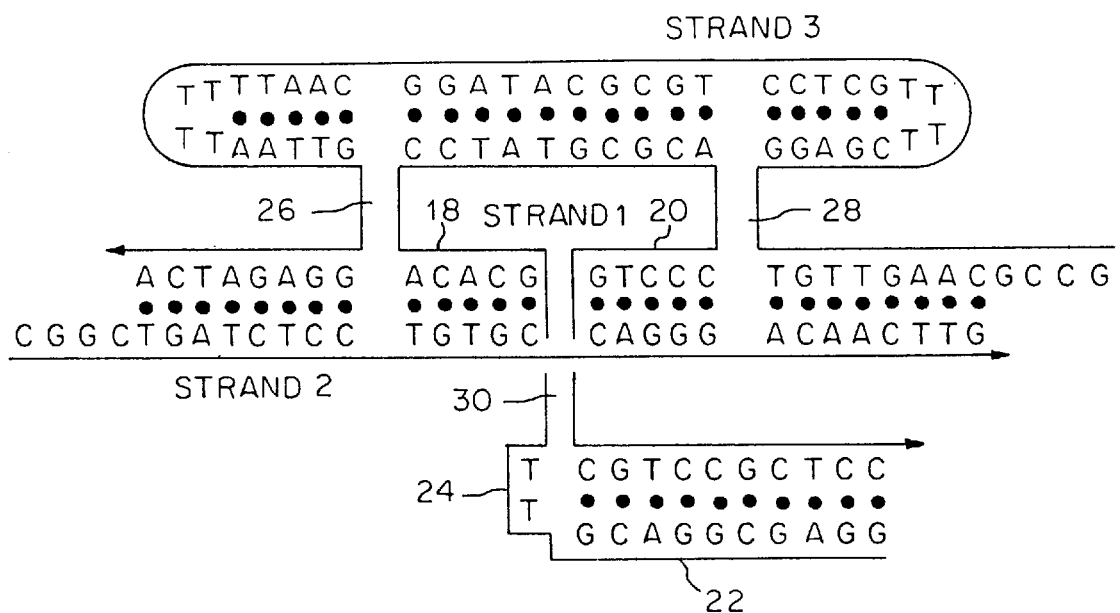
FIGS. 4A and 4B illustrate the strands used to assemble a DAE molecule with a bulged junction. The d(CGGC)

sequence at the 5'-end of strand 2 (SEQ ID NO:2) was transposed to the 3'-end of strand 2 to give strand 2a (SEQ ID NO:3) presented in FIG. 4B, which can be used in place of strand 2 to form a DAE molecule. The nucleotide sequence of strands 3 and 1a in FIG. 4A correspond to SEQ ID NO:4 and SEQ ID NO:1 respectively.

Figure 5A:
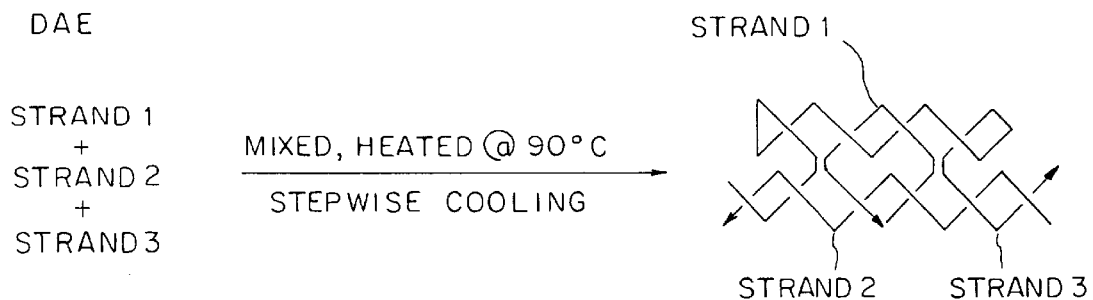
Figure 5B:
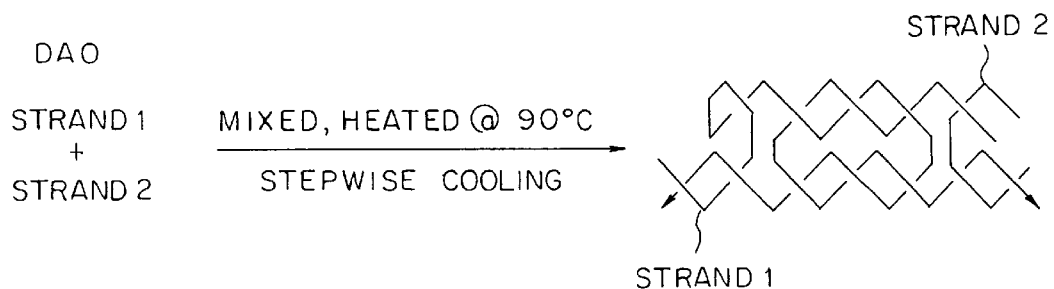

FIGS. 5A and 5B schematically show the protocol for construction of DAE (FIG. 5A) and DAO (FIG. 5B) molecules.

Figure 6:
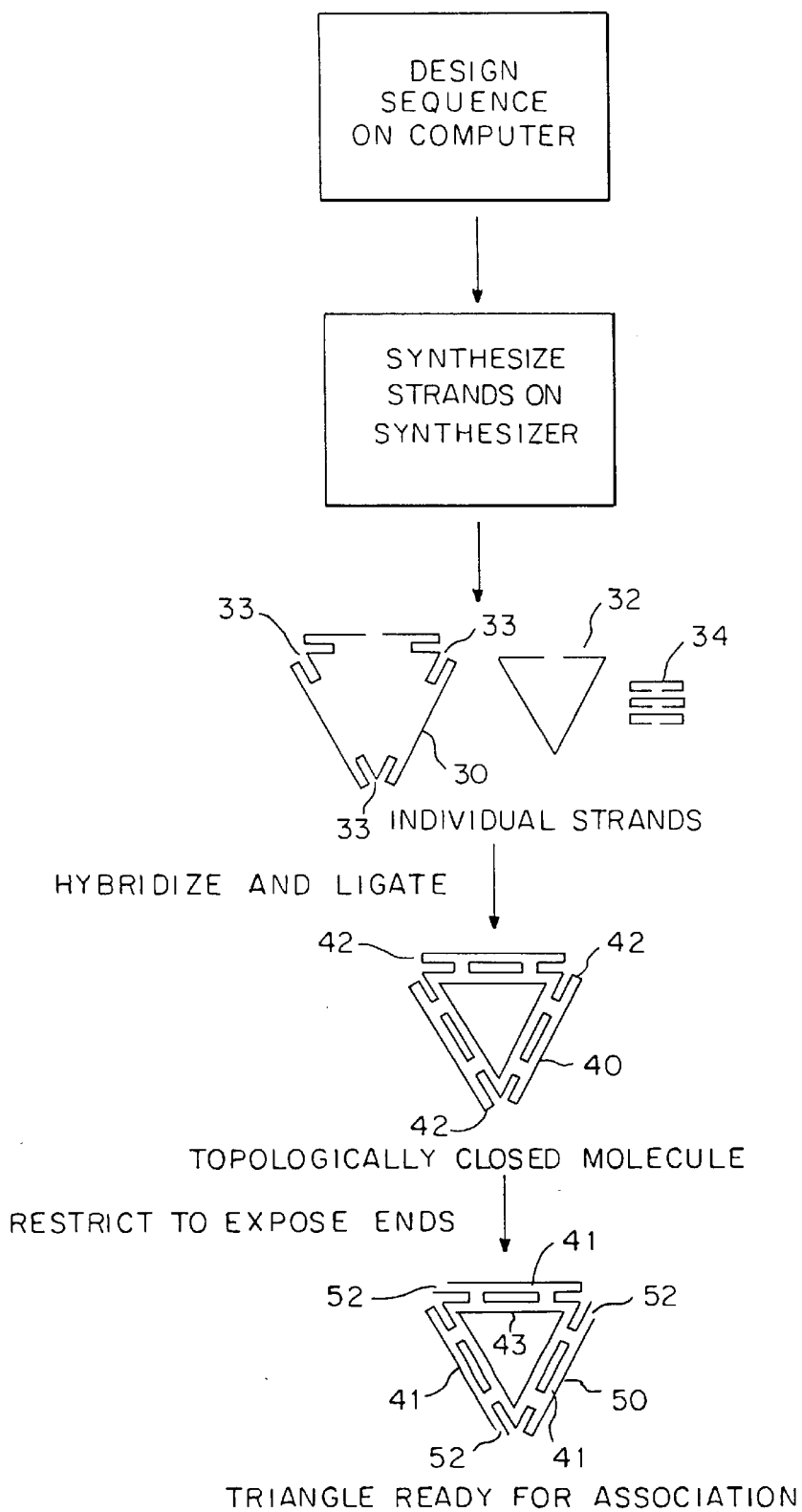

FIG. 6 schematically shows the protocol for producing a topologically closed nucleic acid structure and preparing such a structure for assembly into a symmetrical polynucleic acid structure.

Figure 7A:
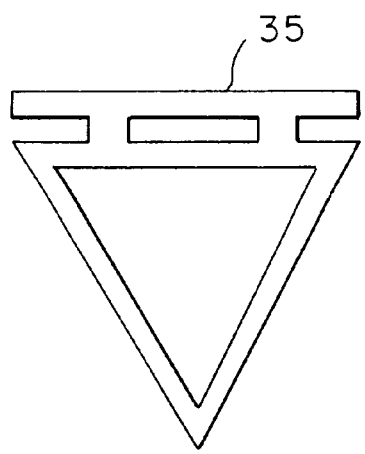
Figure 7B:
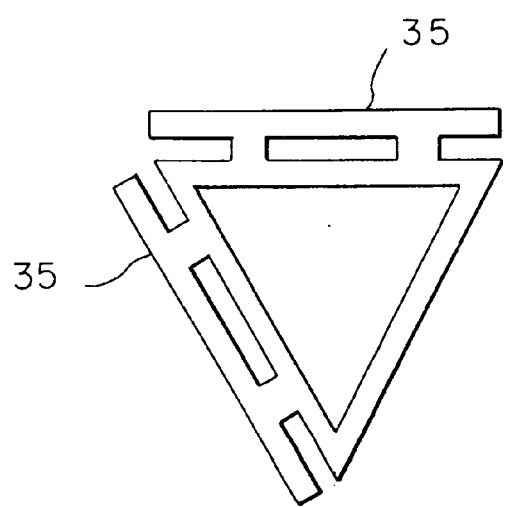

FIGS. 7A and 7B shows topologically closed nucleic acid structures having one or two antiparallel double crossover molecule(s), respectively.

Figure 8:
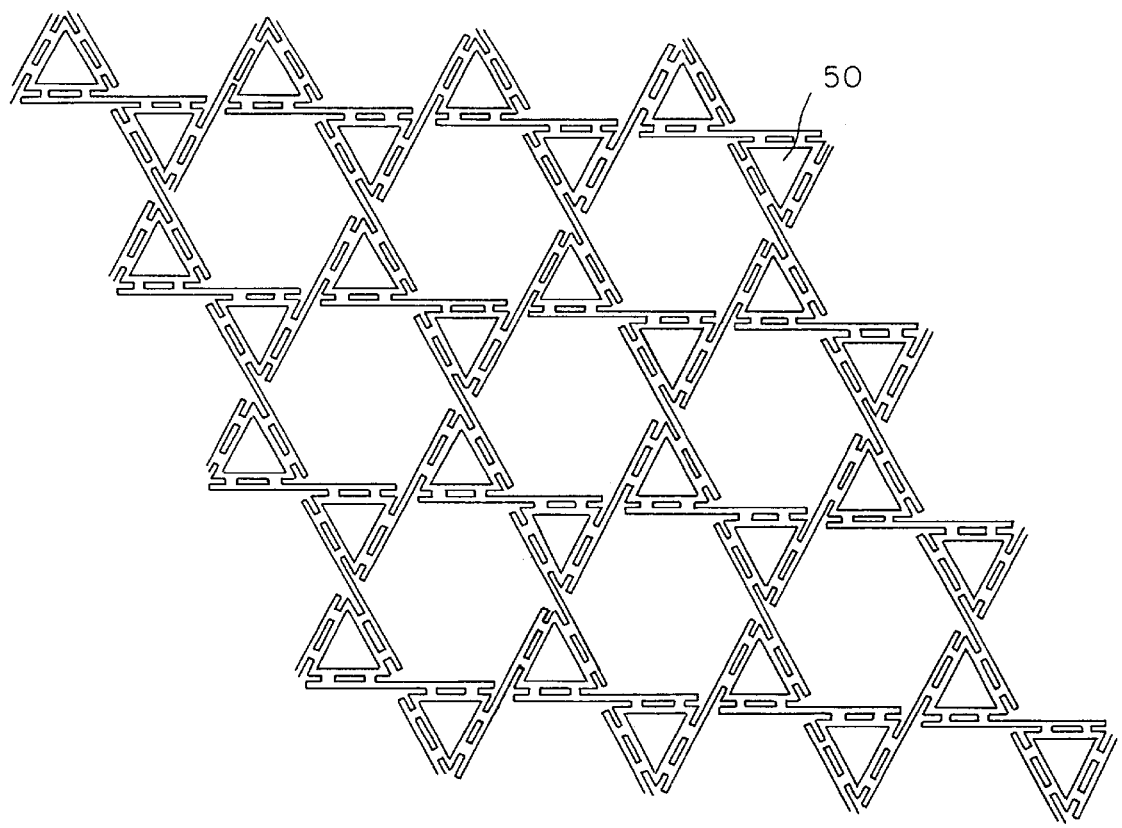

FIG. 8 illustrates a two dimensional lattice that can be constructed from the topologically closed molecule shown in FIG. 6 and treated with a growth enzyme prior to construction.

Figure 9:
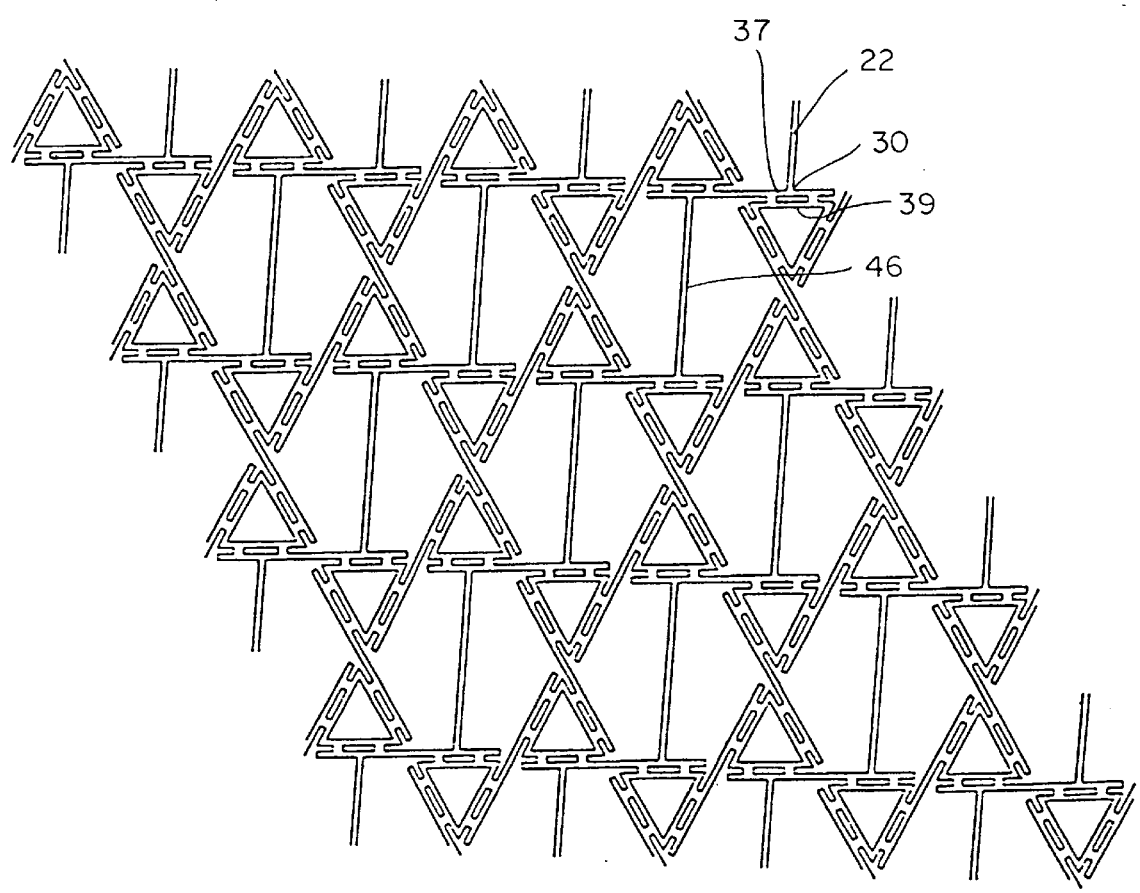

FIG. 9 illustrates a two dimensional lattice similar to FIG. 8, but containing DAE molecules with a bulged junction.

Figure 10A:
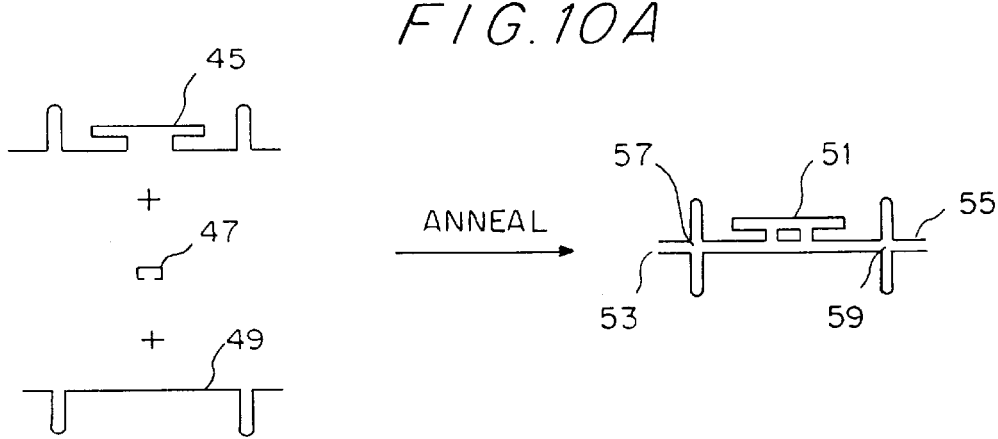
Figure 10B:
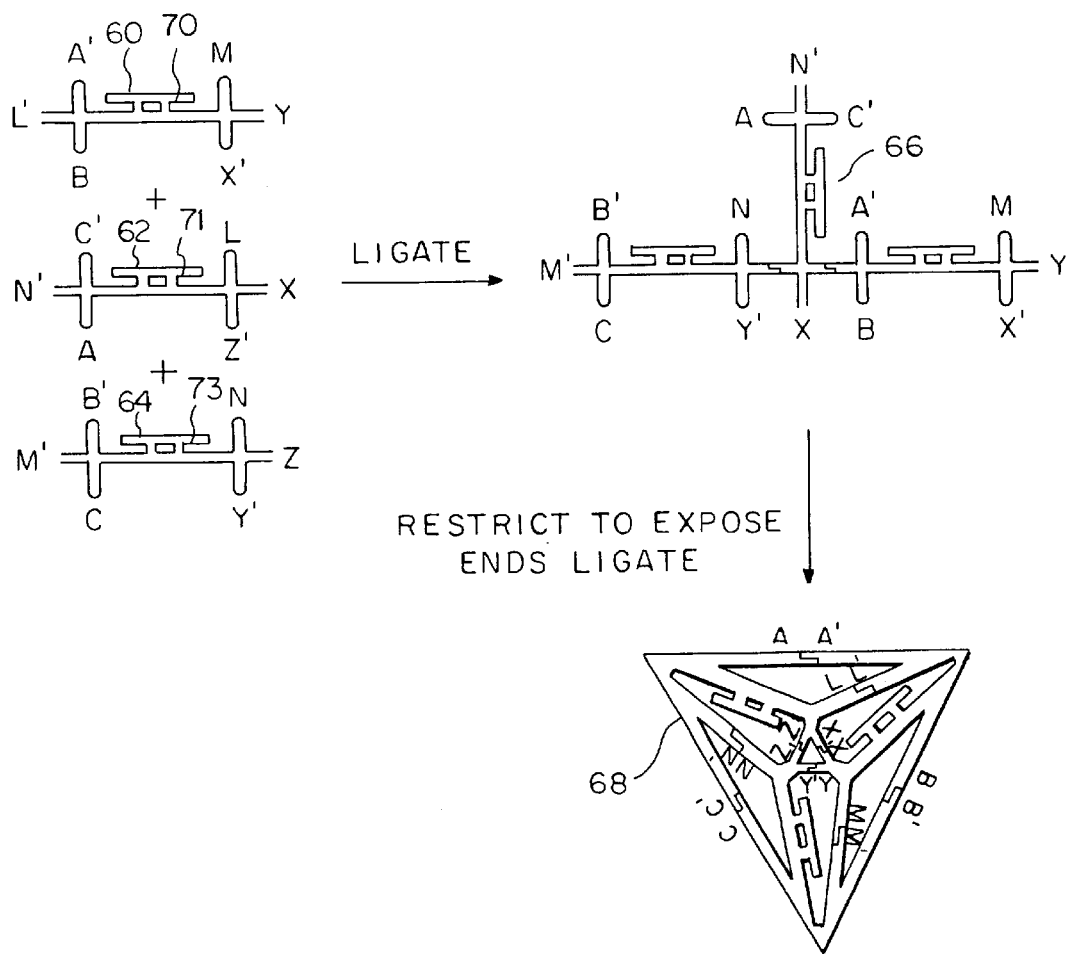

FIGS. 10A and 10B schematically show the protocol for producing an octahedron as a polynucleic acid structure. FIG. 10A illustrates the construction of an antiparallel nucleic acid double crossover monomeric molecule and FIG. 10B illustrates the assembly of monomeric antiparallel nucleic acid double crossover molecules into an octahedron (shown as a Schlegel diagram).

Figure 11A:
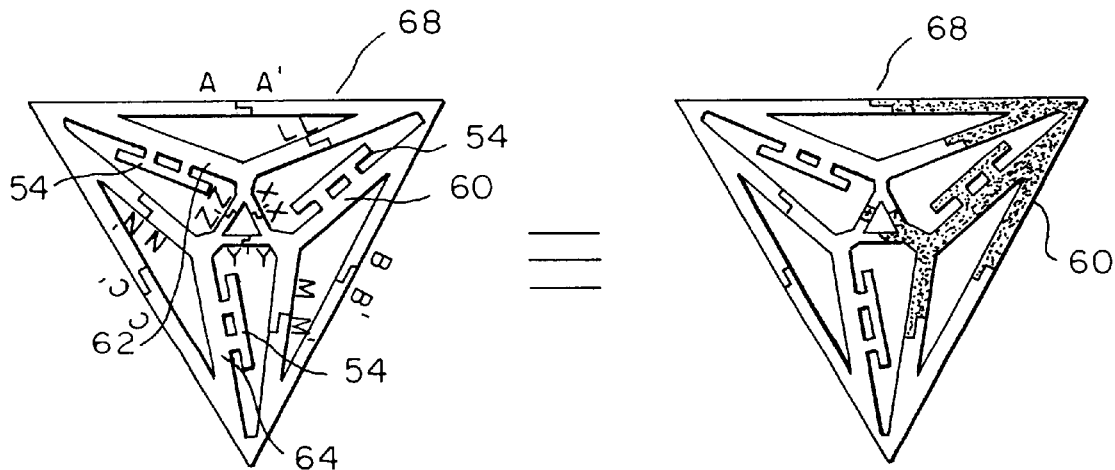
Figure 11B:
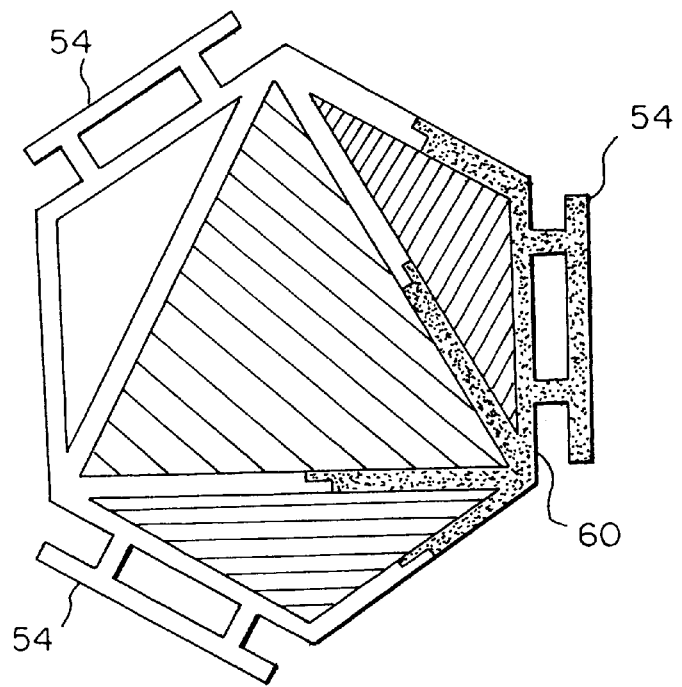

FIGS. 11A and 11B are two different representations of the same octahedron molecule where FIG. 11A is a Shlegel diagram and FIG. 11B is a plan view. One monomeric unit of antiparallel nucleic acid double crossover molecule is shown by the region of solid black.

FIG. 12 schematically illustrates the construction of a tetrahedron from two antiparallel nucleic acid double crossover molecules.

FIG. 13 illustrates antiparallel nucleic acid double crossover molecules as monomeric units in the construction of an icosahedron represented in Schlegel diagram form.

Figure 14A:
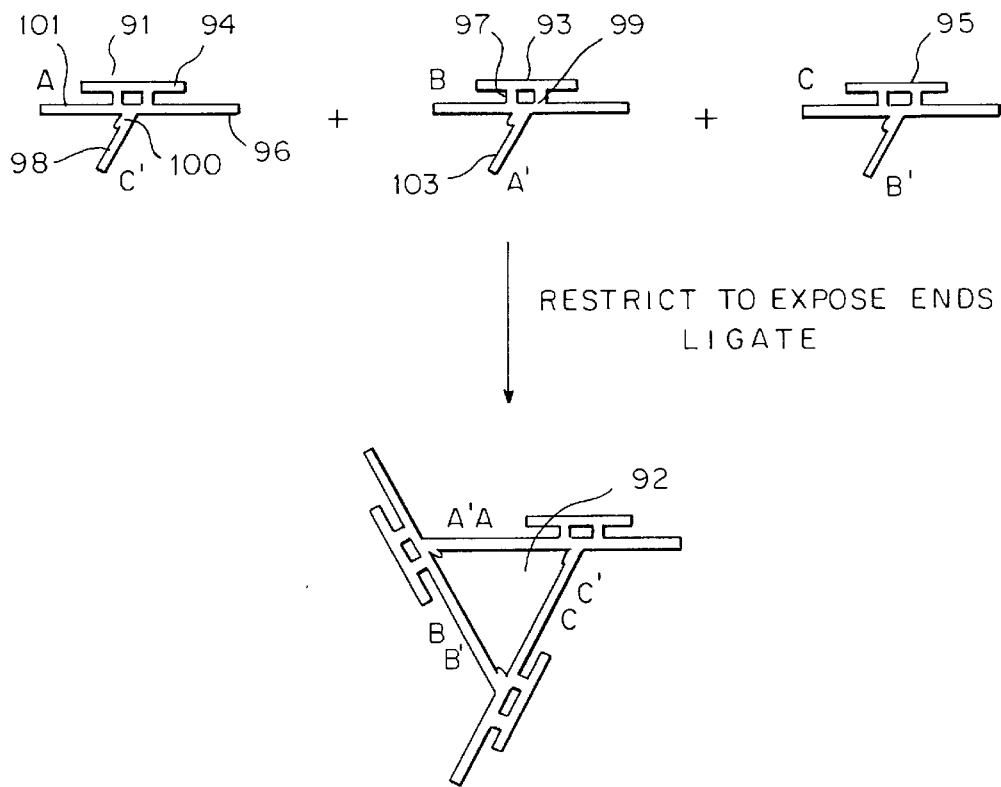

FIG. 14A schematically shows the protocol for producing a nucleic acid triangle with buttressed junctions.

Figure 14B:
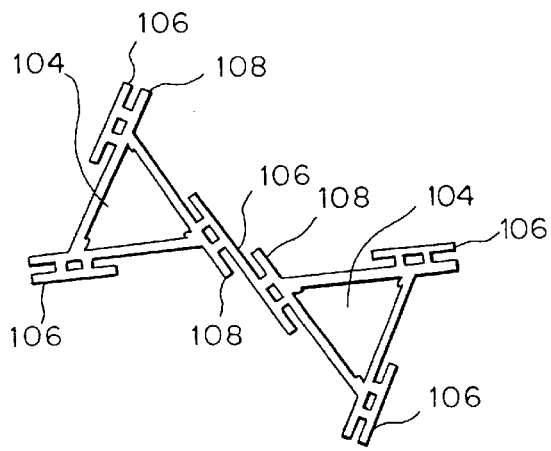
Figure 14C:
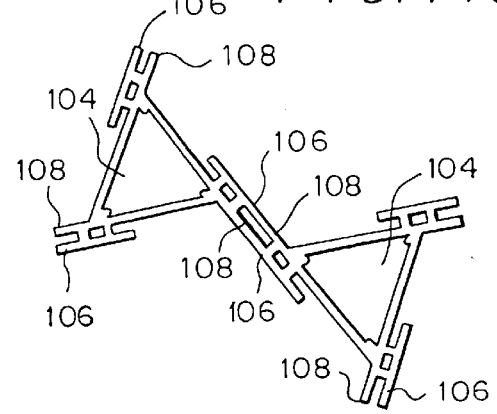

FIGS. 14B and 14C shows examples of how two buttressed triangles can be connected together.

Figure 15:
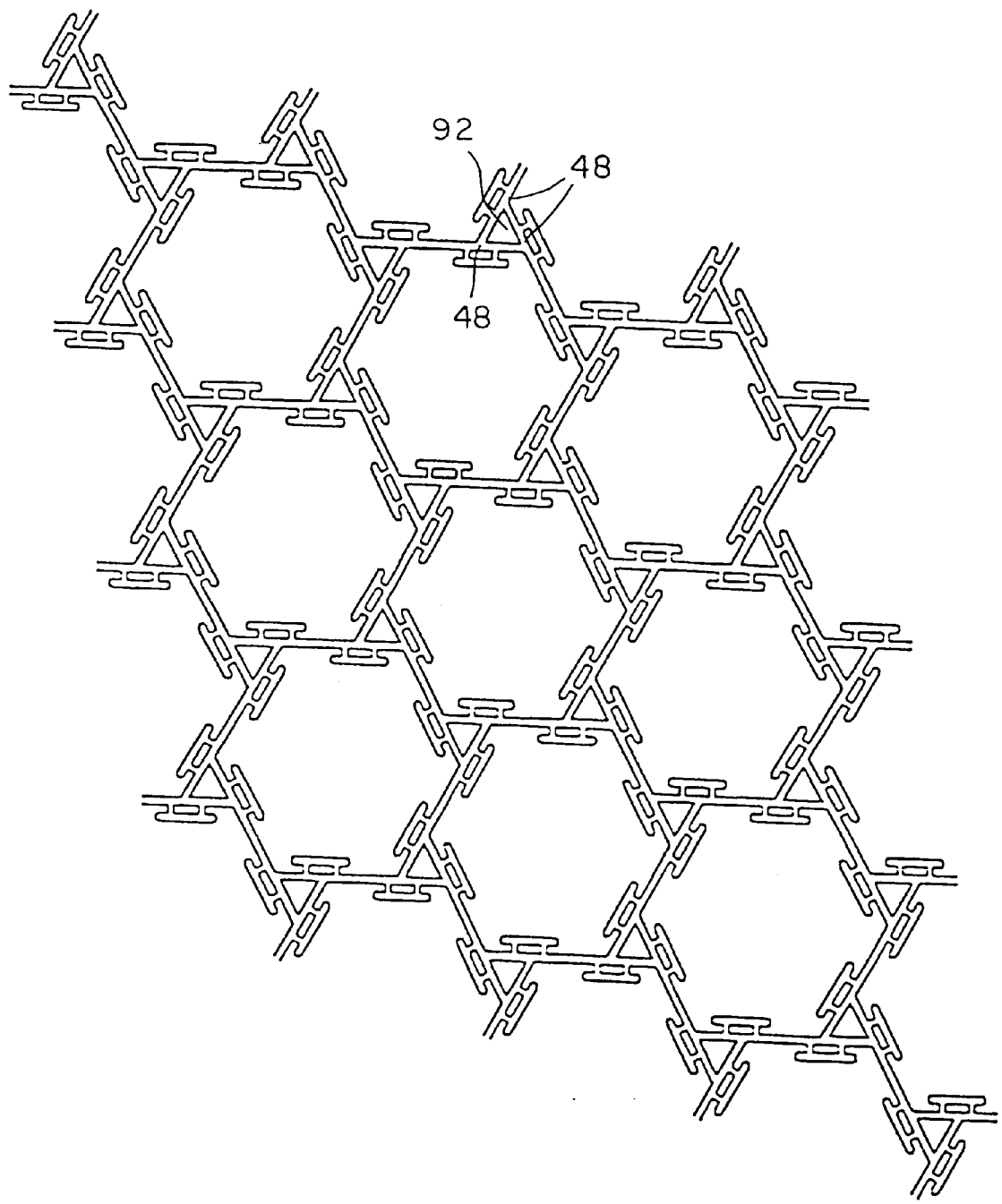

FIG. 15 illustrates a two dimensional lattice constructed from nucleic acid triangles with buttressed junctions.

Figures 16A, 16B:
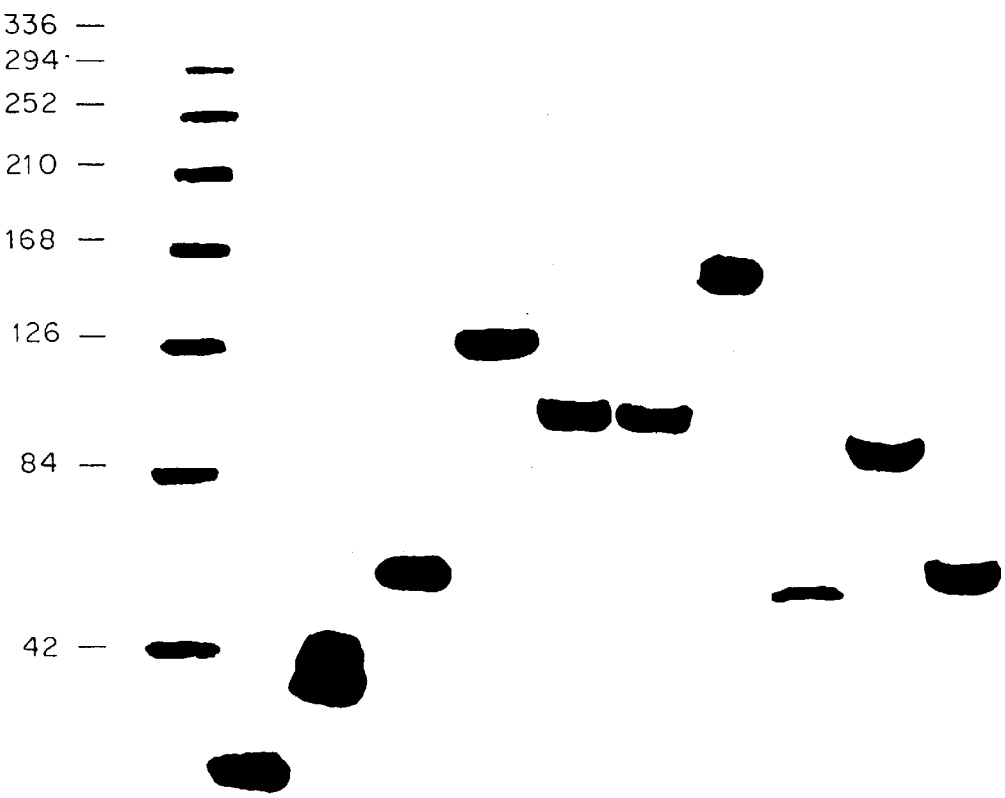

FIGS. 16A and 16B illustrate a non-denaturing gel containing the constituents of the DAE molecule studied in this example 1. The strands contained in the samples applied to the non-denaturing polyacrylamide gel are indicated in FIG. 16A and a drawing of the visualized gel is illustrated in FIG. 16B. Lanes 1–4 contain single strands 1 (with the bulged junction), 1a (without the bulged junction), 2a (cyclically permuted to eliminate the sticky end), and 3. Strand 1 forms a ladder of 42-mers, that help to calibrate the gel. Lane 5 contains the trimer of strands 1, 2a and 3, similar to the DAE molecule with a junction, but with the sticky ends rephased, so that the molecule is well-behaved on this gel (see strand 2a of FIG. 3). Lane 6 contains the DAE molecule without an extra junction, and lane 7 contains the doubly nicked version of that junction; the nick on the central strand faces the nick in the strand 3 (generated by using two shorter strands, 3a and 3b) here. Both lanes 6 and 7 contain the rephased version of strand 2 (strand 2a) used in lane 5. Lane 8 contains the unrephased version of strand 2, and its cohesion is seen to make characterization of the molecule difficult. Lane 9–11 contain mixtures of the strands in which one strand has been omitted.

Figure 3A:
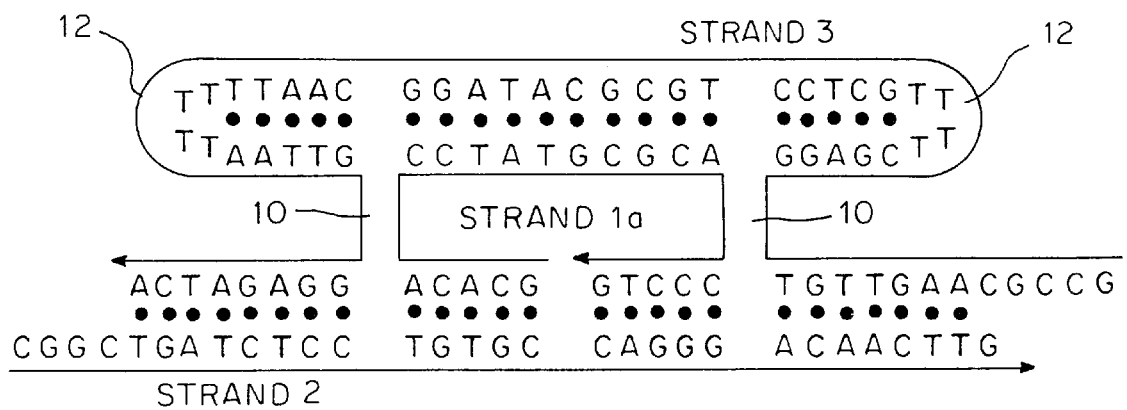
FIGS. 3A and 3B illustrate the strands used to assemble the DAE molecules. The d(CGGC) sequence at the 5'-end of strand 2 (SEQ ID NO:2) was transposed to the 3'-end of strand 2 to give strand 2a (SEQ ID NO:3) presented in FIG. 3B, which can be used in place of strand 2 to form a DAE molecule. The nucleotide sequence of strands 3 and 1a in FIG. 3A correspond to SEQ ID NO:4 and nucleotides 13 to 32 of SEQ ID NO:1.

FIGS. 17A and 17B show the hydroxyl radical cleavage patterns of a conventional DAE molecule where the densitometer traces for each strand are shown in FIG. 17A above a summary drawn of the sequence of the DAE molecule as presented in FIG. 17B. Each panel of FIG. 17A shows the densitomer trace of the strand labeled at the top. The double strand (DS) is compared with the double crossover (DC). The arrows indicate the sites of the crossovers. Residues are numbered at every tenth position. In FIG. 17B, sites of greater protection are indicted by large triangles, and sites of lesser protection are marked by small triangles. The sequences are the same as shown in FIG. 3A.

Figure 18A:
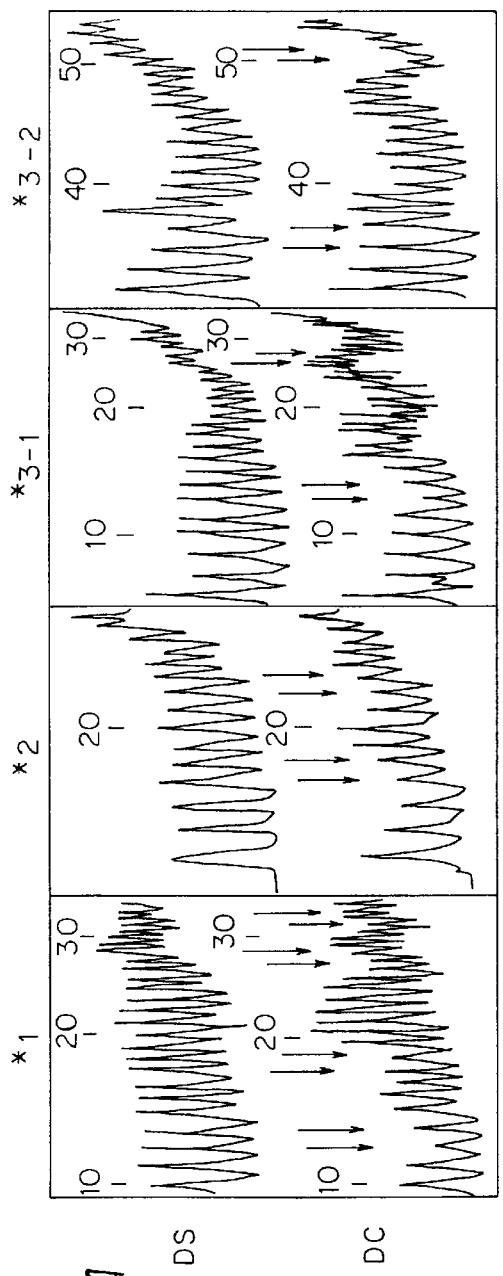
Figure 18B:
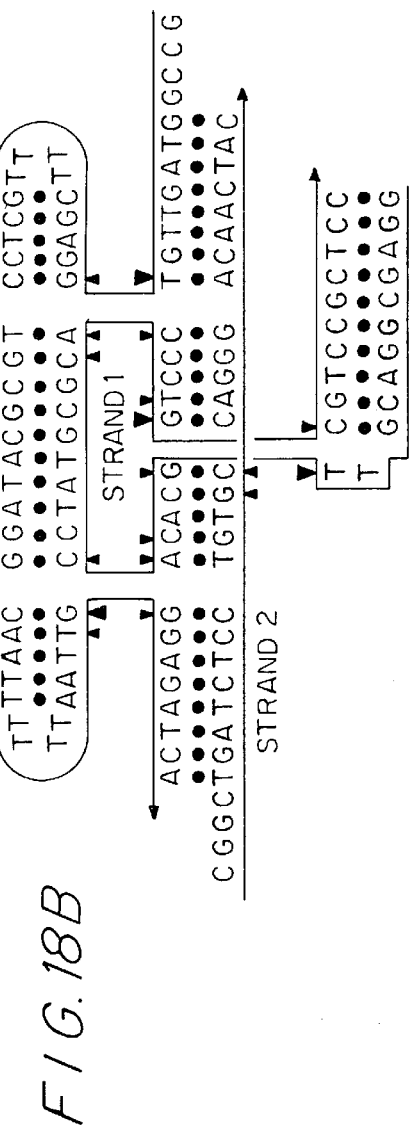

FIGS. 18A and 18B show the hydroxyl radical cleavage patterns of a DAE molecule containing a bulged 3-arm branched junction. The same conventions apply as in FIGS. 17A and 17B. A protection pattern similar to that in FIGS. 17A and 17B is seen in the corresponding residues, although it is of somewhat lower intensity. In addition, the site near the extra junction also shows protected nucleotides. The sequences of FIG. 18B is the same as shown in FIG. 4A.

FIGS. 19A and 19B show the ligation of DAE molecules where FIG. 19B is a drawn illustration of an autoradiogram of a denaturing gel and FIG. 19A indicates the types of molecules treated with the specified enzymes and electrophoresed in the lanes on polyacrylamide gel. Lanes 1 and 2 contain a standard 3-arm branched junction, 'JY21', that generates linear and circular markers; lane 2 has been treated with exonucleases, to yield only a 21-mer single-stranded circular DNA ladder. Linear markers are indicated by the suffix 'L', and single-stranded cyclic markers are indicated by the suffix 'C'. Lanes 3–8 contain the DAE molecule (3–6) or its doubly nicked version. The column heading 'DX' refers to double crossover molecules. A fixed amount of a cyclic 42-mer has been added to each of lanes 3–8, so that the intensity of each lane can be compared directly, regardless of the total radioactivity of the lane. Lanes 3 and 5 contain ligation ladders of labeled strand 2 of the DAE molecule, lanes 4 and 6 have been treated with exonucleases I and III, and lane 6 has also been treated with Hha I restriction endonuclease. No cyclic material is visible in these lanes. Any that appeared in lane 4 would correspond to single strand ligations, rather than double strand ligations; those can only be revealed if the molecule has been restricted to cleave strand 3. The molecule with two nicks, constituting two linked junctions, but not a double crossover shows cyclization as the dimer, with a visible ladder extending to at least the 180-mer near the top of the gel.

Figures 20A, 20B:
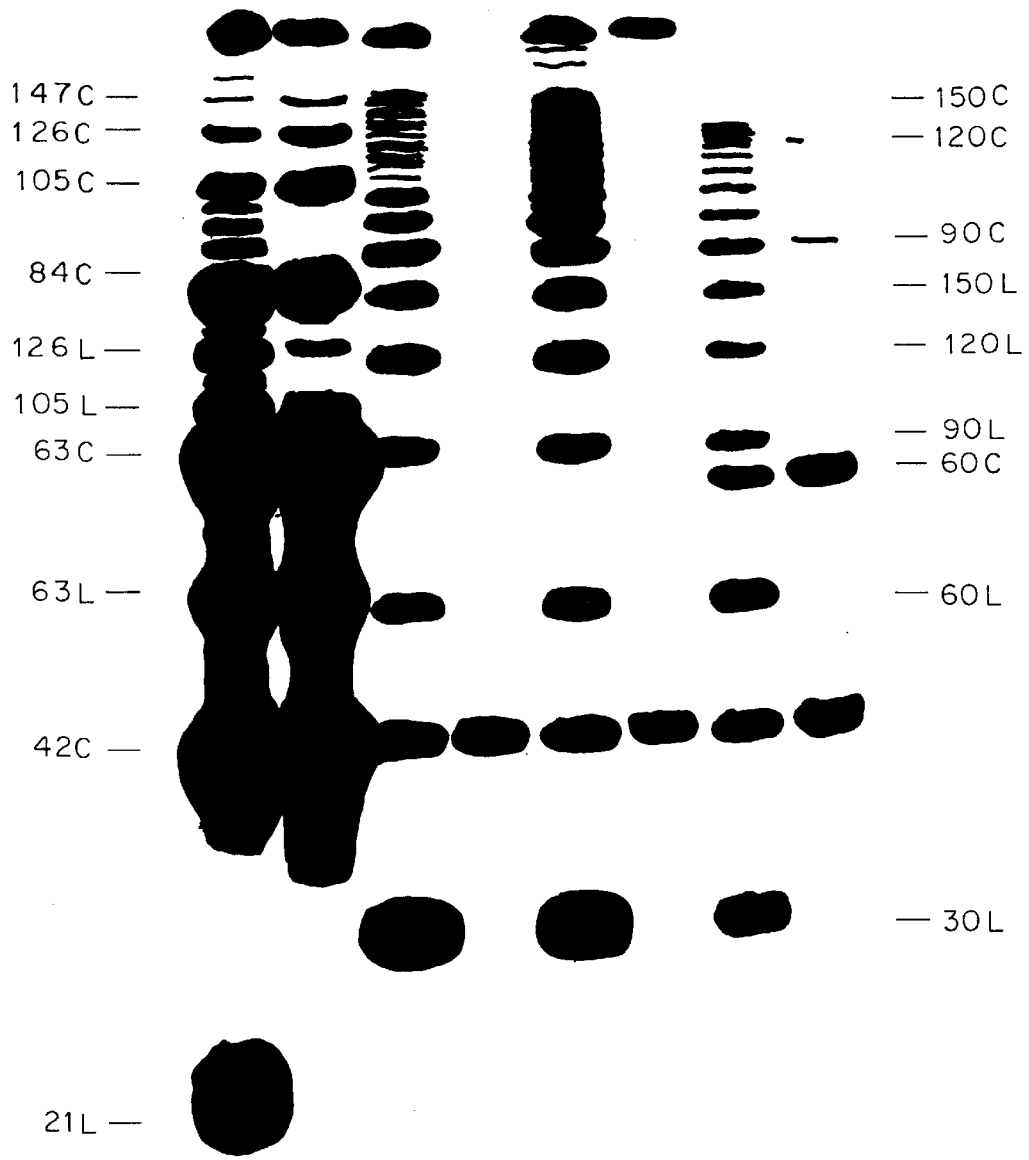

FIGS. 20A and 20B show the ligation of a DAE molecule containing an extra bulged 3-arm junction. The same conventions apply here as in FIGS. 19A and 19B. In contrast to the conventional DAE molecule, a small amount of a single-stranded circular ladder is seen in lane 4, corresponding to cyclic dimers, trimers, etc. Faint quantities of these bands are also visible in lane 6. Thus, a small amount of cyclization is present with this molecule that is absent from the conventional DAE molecule. Nevertheless, the amount of cyclization is much less than with conventional branched junctions, as seen in lane 8.

Figure 21:
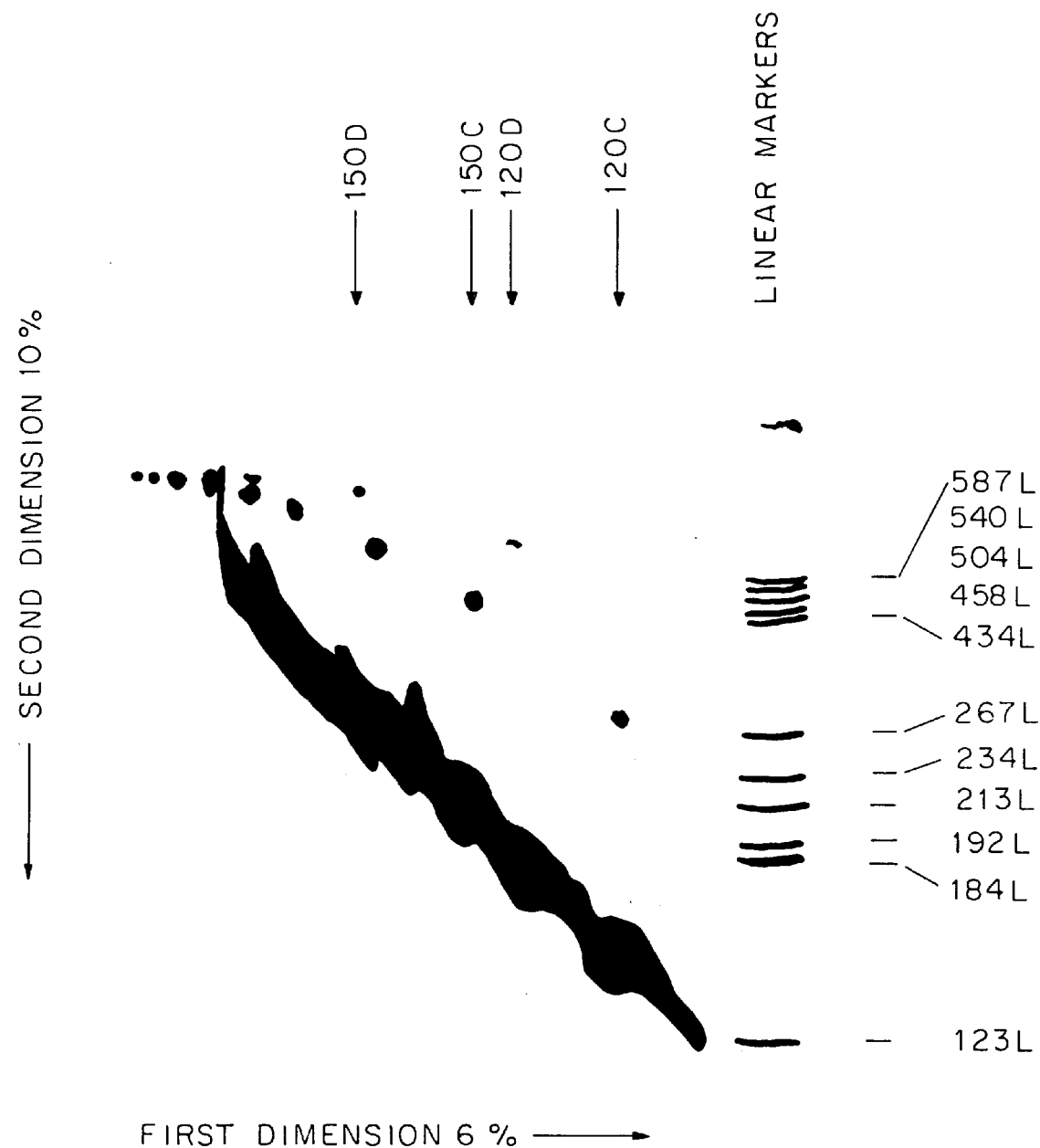

FIG. 21 is a drawn illustration of the products of ligating a 30-nucleotide duplex with the same sequence as the ligation domain of the DAE molecules as visualized on an autoradiogram of a two-dimensional (6%, then 10%) polyacrylamide denaturing gel. A ladder of linear markers has been run in the second dimension. Linear molecules run on the diagonal, single-stranded circles in the arc above it, and duplex circles in the second arc above the first one. Molecular identities are marked as follows: Linear DNA, 'L', single-stranded circles, 'C', duplex circles, 'D'. The faint spot at the right of the duplex arc is a 120-mer circle. The spot to its left is a 15-mer circle, whose size is characterized in FIG. 22 below. The 120-mer circle is reproducible, indicating that this sequence has no problem forming small circles.

Figure 22:
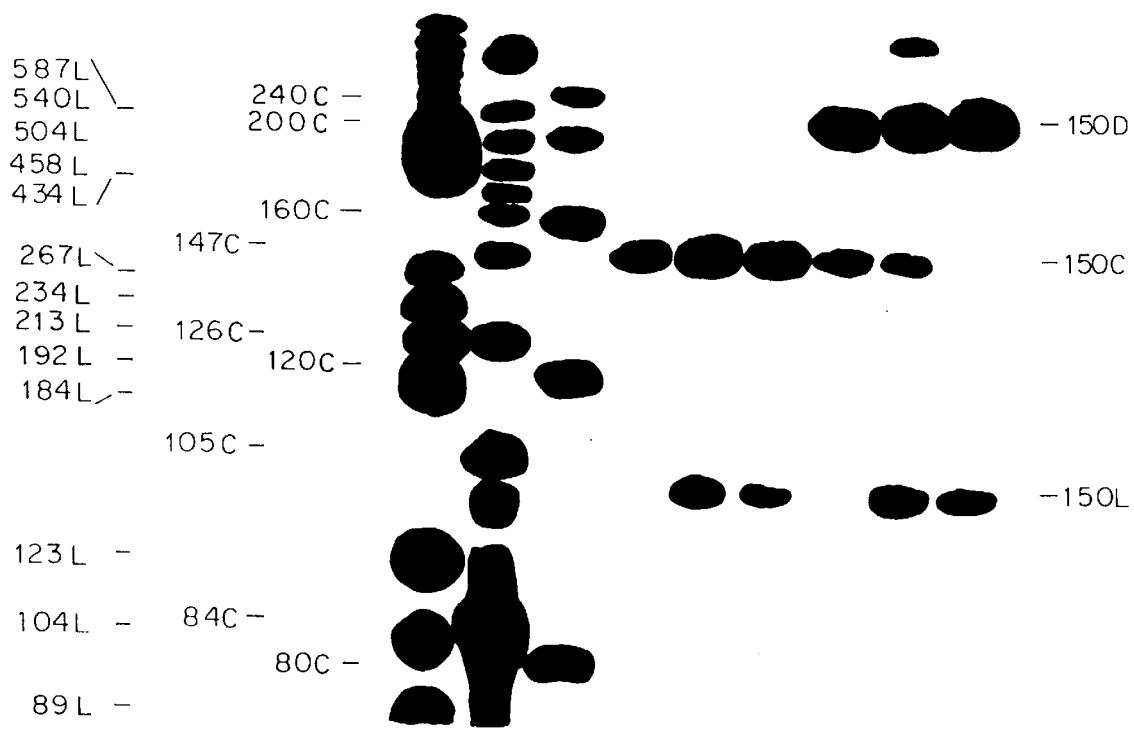

FIG. 22 is a drawn illustration of the characterization of the 150-mer circle, as visualized on a denaturing gel analyzed on a BioRad GS-250 Molecular Imager. The labeling conventions of FIG. 21 are retained. Lanes 1–3 contain ladders of linear markers, the 21-mer single-stranded circular ladder of FIGS. 20A and 20B, and a 40-mer single-stranded circular ladder (Petrillo et al, 1988, supra). Lanes 4–6 contain a single-stranded 150-mer circle extracted from the gel in FIG. 21. The material in lane 6 is untreated, the material in lanes 4 and 5 has been heated to 90° C. for 10 minutes, and the material in lane 4 has also been treated with exonucleases I and III. The material in lanes 7–9 corresponds to the putative 150-mer circle of FIG. 21. The material in lane 9 is untreated, the material in lanes 8 and 7 has been heated 90° C. for 10 minutes, and the material in lane 7 has also been treated with exonucleases I and III. It is clear that the material in lane 9 breaks down to single-stranded circle (in lanes 8 and 7), similar to the material in lane 6, as well as generating some linear material. This shows that this band is a 150-mer duplex circle.

DETAILED DESCRIPTION OF THE PREFERRED EMBODIMENTS

The polynucleic acid structures of the present invention are polynucleic acids that are assembled to form branched multimers of repeating units composed at least partially of antiparallel double crossover molecules in accordance with the method of the present invention. A plurality of antiparallel double crossover molecules, which are linked to form a basic unit of a rigid nucleic acid motif, such as a nucleic acid triangle, are assembled from single stranded oligonucleotides or polynucleotides to produce the polynucleic acid unit molecules of the present invention. Similarly, more complex polynucleic acid structures of the present invention having two dimensional or three dimensional periodic lattices with symmetrical intermolecular contacts (translational symmetry) are assembled from basic units of linked antiparallel double crossover molecules.

DNA molecules containing two crossover sites between helical domains have been widely suggested as intermediates in recombination processes involving double stranded breaks. Accordingly, "double crossover molecules" are those nucleic acid molecules containing two branched junctions (Holliday junctions corresponding to the crossover sites) linked together by ligating two of their double helical arms. By branched junction is meant a point from which three or more helices (arms) radiate.

There are five isomers of double crossover molecules (Fu et al., *Biochemistry* 32: 3211–3220, 1993), which fall into two broad classes of molecules differentiated by the relative orientations, parallel (DP) or antiparallel (DA), of their helix axes. As parallel double helical molecules are usually not well behaved, antiparallel isomers of double crossover molecules are then the building block components intended to be used in the present invention.

Figure 1A:
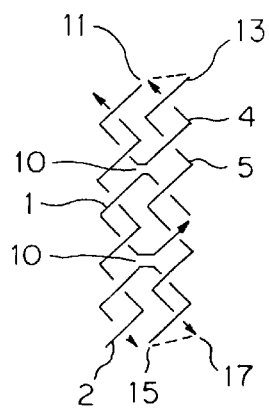
FIGS. 1A and 1B show a schematic representation of two types of antiparallel double crossover molecules, DAE (FIG. 1A), with an even number of double helical half-turns between the crossover, and DAO ((FIG. 1B), with an odd number of half-turns between the crossovers. The DAE molecule as illustrated contains five strands, two of which are continuous, or helical strands, drawn with thick lines, and three of which are crossover strands, drawn with thin lines, including the cyclic strand in the middle. The 3' ends of each strand are indicated by an arrowhead. The DAO molecule is depicted to the right of the DAE molecule, and it contains only 4 strands. Two of these are drawn with thick lines and two with thin lines. The twofold symmetry element is perpendicular to the page, vertically, for the DAE molecules, and it is horizontal within the page, for the DAO molecule. Thick lines are symmetrically related to thick lines and thin to thin lines in the DAE molecule, whereas thick lines are related to thin lines by symmetry in the DAO molecule. Sealing the cyclic strand in the middle of the DAE molecule would be necessary for the symmetry to be exact for that molecule.
Figure 1B:
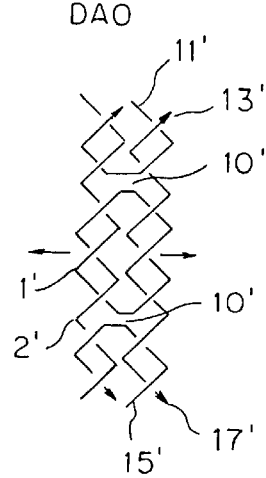

In order to avoid torsional stress on the double crossover molecules, the distance between the branched junction or crossover points are specified as either even (E) or odd (O) multiples of half helical turns. Antiparallel double crossover molecules with an even number of half helical turns between crossover points are designated DAE and those with an odd number are designated DAO. FIGS. 1A and 1B show schematic representations of the DAE and DAO forms, respectively, of antiparallel double crossover molecules in which two strands of a helix are presented as a pair of thick and thin lines. The DAE and DAO molecules depicted in FIGS. 1A and 1B have strands 1, 2, 4 and 5 and strands 1' and 2' respectively. There are two half helical turns between the two crossover points (10) in the DAE molecule depicted and three half helical turns between crossover points (10') in the DAO molecule.

Figure 2A:
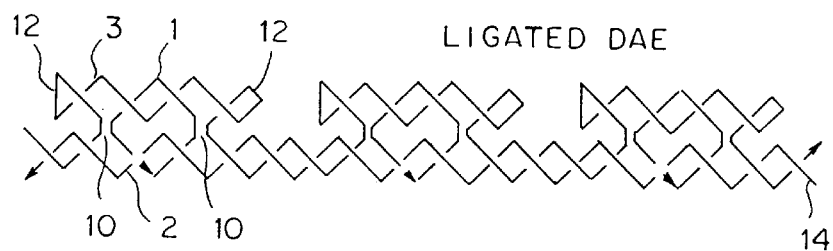
FIGS. 2A and 2B show schematic representations of ligated antiparallel double crossover molecules in which one helical domain has been sealed by hairpin loops, and then the molecules have been ligated together. The ligated DAE (FIG. 2A) molecule contains a reporter strand, drawn with a thick line. By contrast, the ligated DAO (FIG. 2B) molecule is a series of catenated molecules, which are drawn here with alternating thick and thin lines. Note that under denaturing conditions the ligated DAE molecule would be a catenane of two strands if it were to cyclize.
Figure 2B:
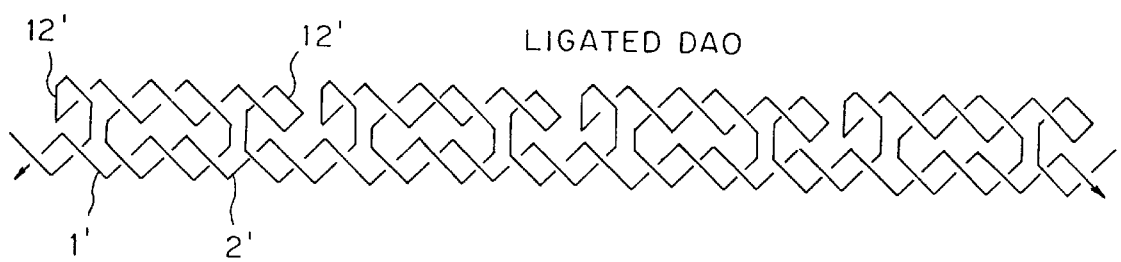

In the present invention, it was discovered that monomers of either DAE or DAO double crossover molecules can be ligated extensively without showing a propensity to cyclize indicating that the resulting ligation products were structurally stiff. Examples of ligated DAE and DAO molecules are presented schematically in FIGS. 2A and 2B. The DAE and DAO monomers ligated as shown in FIGS. 2A and 2B contain two closed ends 12 for DAE and 12' for DAO. These are formed by joining ends 11, 13 and 15, 17 of the DAE molecule of FIG. 1A and ends 11', 13' and 15', 17' of the DAO molecule of FIG. 1B into hairpin loops.

Apart from the number of half helical turns between crossover points, the ligated DAE and the ligated DAO molecules shown in FIGS. 2A and 2B, respectively, are also differentiated by the ligated DAE molecule having a reporter strand, designated by the reference numeral 14 (strand 2) and the ligated DAO molecules being a series of catenated molecules, represented as alternating closed thick (strand 2') and thin (strand 1') lines. As used here, a reporter strand is a strand of nucleic acid whose fate in a test or assay represents the fate of the entire nucleic acid molecular complex (ligation product). For example, the thick line presented in the ligated DAE product (FIG. 2A) is the reporter strand 14 because its initial 30 nucleotide length (strand 2 in FIG. 3) is extended by 30 nucleotides every time a new double crossover monomer is ligated to the growing molecular complex. Likewise, if the molecular complex were to cyclize, the reporter strand would also cyclize. Thus, the reporter strand provides the advantage whereby it is much easier to characterize the fate of the molecular complex by the fate of the reporter strand than by the entire complex itself.

Referring to FIG. 3A, three single strands, such as 1a, 2 (or 2a in FIG. 3B), and 3, can be designed so that their sequence complementarity allows the formation of a DAE molecule having two closed ends 12. Thus, two free ends of a DAE molecule (11, 13 and 15, 17 in FIG. 1A) can be closed as shown in FIG. 2A by designing self-complementary sequences into strand 3 where two hairpin loops 12, corresponding to closed ends, are present in place of the free ends 11, 13 and 15, 17 shown in FIG. 1A.

Figure 3B:
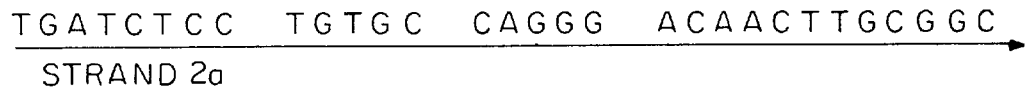

FIGS. 4A and 4B illustrate another example of a DAE molecule to be used as a building block component of the nucleic acid structures and polynucleic acid structures of the present invention. Strands 2, 2a and 3 are the same as shown in FIGS. 3A and 3B, but strand 1 has additional nucleotides both 5' and 3' to strand 1a of FIG. 3A. Thus, strand 1 as presented in FIG. 4A has three arms 18, 20, 22 and a bulged arm 24. The structure of FIG. 4 has three branched junctions 26, 28 and 30, of which branched junction 30 is also a bulged junction.

DAE and DAO molecules having two closed ends can be constructed by the method outlined in FIGS. 5A and 5B. In this method, two or three single stranded polynucleotides are mixed together and heated at a temperature above the melting or denaturation temperature of the complementary strands, e.g. 90° C., to eliminate any initial secondary structures present in the mixture, and then cooled in a stepwise manner to allow the strands to anneal based on sequence complementarity. This is also the method in which the DAE ligation products analyzed in Example 1 below are produced.

Besides ligating together monomeric DAE and DAO together in a linear fashion as shown in FIGS. 2A and 2B, the polynucleic acid structures of the present invention, used as the basic rigid motif units for assembling more complex two dimensional polynucleic acid structures, can also be formed in a different manner. One example of a protocol for forming such basic units of rigid topologically closed molecules, which can then be prepared for assembly into complex symmetrical polynucleic acid structures, is illustrated in FIG. 6. The individual single stranded oligonucleotides or polynucleotides to be hybridized are first designed and synthesized.

The single stranded polynucleotide 30 shown in FIG. 6 has bulges 33 (i.e., $dT_6$ bulges) forming the vertices of a triangle so that the polynucleotide strand 30 in FIG. 6 can assume a triangular shape. Polynucleotide strand 32 either also has bulges to form the vertices of a triangle or forms a triangle upon being annealed to polynucleotide strand 30. Single stranded polynucleotides 34 as shown in FIG. 6 are copies of strand 1 or 1a as depicted in FIG. 3A and in FIG. 2A.

Afterwards, the individually synthesized single strands are hybridized (denaturing followed by annealing) to form the helices and then ligated to seal gaps in the strands. A topologically closed molecule 40, which is a nucleic acid triangle for the example shown in FIG. 6, results. If the synthesized strand 30 is designed such that hairpin loops 42 contain a predetermined restriction enzyme site, then these sites 42 can be cleaved at the recognition sequence by the predesignated restriction enzyme such that one end 52 of each of the anti-parallel double crossover molecules will be exposed. By exposing cleaved ends 52 on one helical domain 41 of each antiparallel double crossover molecule, the nucleic acid triangles 50, as exemplified in FIG. 6 where the sides, or edges of the triangle are formed by another helical domain 43 a double crossover molecule parallel to helical domain 41, are ready for assembly into a more extensive and symmetrical polynucleic acid structure. Thus, helical domains 41 can be extended by connecting one helical domain 41 of one nucleic acid triangle 50 to a corresponding helical domain 41 of another nucleic acid triangle at their cleaved ends 52.

It should be understood that when synthesizing the single stranded oligonucleotides or polynucleotides for forming the topologically closed nucleic acid structure, the choice of sequence is substantially arbitrary, provided that strands intended to form a hairpin or to be opposite one another are complementary, and further provided that predetermined recognition sites for growth enzymes are designed at predetermined locations in the resultant topologically closed molecule (see U.S. Pat. Nos. 5,278,051 and 5,468,851). It is preferable to use previously described symmetry minimization algorithms (Seeman, *J. Biomol. Str. & Dyns.* 8: 573–581, 1990; Seeman, In: *Biomolecular Stereodynamics,* ed. R. H. Sarma, Academic Press, pp. 269–277, 1981; Seeman, *L. Theor. Biol.* 99: 237–247, 1982) in order to optimize the sequences and incorporate the desired features while avoiding unwanted cross-hybridization or branch migration.

The term "growth enzyme" is intended to mean those enzymes, e.g., restriction enzymes, whose recognition sites are either interrupted, asymmetric, blunt cutting, form symmetric pairs, or are distal to the cutting site. "Growth enzymes" may also include a combination of enzymes, chemicals, or enzymes and chemicals which perform any number of reactions to yield the same results. See U.S. Pat. Nos. 5,278,051 and 5,468,851 which are herein incorporated by reference.

It should also be understood that it is only preferred, but not required, that DAE and DAO molecules have two closed ends to simplify the number of oligonucleotide or polynucleotide strands to be synthesized. If closed ends are not designed into the synthetic strands, then, in the method outlined in FIG. 6 for instance, polynucleotide strand 30 would be divided and synthesized as six separate strands.

The nucleic acid triangle is the first rigid nucleic acid motif to be identified where the rigid nucleic acid component specifies the vectors of double helical axes (and hence the angles between them) within limits of flexibility no greater than those of linear duplex DNA. Using such rigid motifs of nucleic acid molecules prepared by treating topologically closed molecules of antiparallel double crossovers with growth enzymes, two dimensional and three dimensional nanometer-scale polynucleic acid structures having a rigid framework can be constructed. Further examples of nucleic acid triangles are shown in FIGS. 7A and 7B. The nucleic acid triangle of FIG. 7A has only one antiparallel nucleic acid molecule 35 for an edge of the triangle whereas FIG. 7B has two edges of the triangle formed by antiparallel nucleic acid double crossover molecules 35.

By a "rigid framework", it is intended to mean a structure of vertices and edges whose vertices are not capable of moving relative to each other when its edges are connected to the vertices by swivel joints permitting rotation about the vertex in any direction as defined by Kappraff, In: *Connections,* McGraw-Hill, New York, pp. 270–273, 1990. It can be shown for the three dimensional case that a convex polyhedron is rigid if and only if each of its faces is a triangle (Kapraff, 1990, supra; Seeman et al., 1982, supra).

One embodiment of a two dimensional lattice is presented in FIG. 8, which shows a series of equilateral triangles 50 whose sides are antiparallel double crossover molecules. These triangles have been assembled into a hexagonally-symmetric two dimensional lattice by ligating nucleic acid triangles 50 prepared as shown in FIG. 6, and linking them so as to tile a plane. The linked nucleic acid triangles retain their angular distributions, representing eccentric trigonal valence clusters of nucleic acids.

A second embodiment of a two dimensional lattice is presented in FIG. 9. This two dimensional lattice is also composed of a series of equilateral triangles assembled into a hexagonal symmetry. However, every third side of the nucleic acid triangle units is a DAE molecule with a bulged junction 30 located between the two crossover sites in the DAE molecule, like the DAE molecule shown in FIG. 4A with the crossover sites designated by reference numerals 26 and 28. The two dimensional lattice of FIG. 9. shows pairs of triangles having a bulged junction directly opposed to one another so that an extended arm 22 of a bulged junction can meet and be joined with the corresponding extended arm from its pair to form a connecting arm 46. While the structural symmetry of the lattice decreases by adding an extra arm to every third nucleic acid triangle in the lattice, nevertheless, the extra arm is not a fundamental part of the lattice and does not affect the integrity of the lattice itself.

The lattice of FIG. 9 still retains translational symmetry of its contact points.

Moreover, the extended arm can be used to attach other molecules of interest, such as chemical or biologically active molecules, binding molecules, etc., and can be distorted as needed to accommodate the molecule of interest. For instance, the extended arm 22 can emanate from the junction 30 at virtually any angle relative to the two parallel helical domains 37 and 39.

An extension of the protocol for assembling two dimensional polynucleic acid structures can be carried forward as a protocol for the assembly of three dimensional polynucleic acid structures such as polyhedrons. An example of the construction of an octahedron as a three dimensional polynucleic acid structure is presented in FIGS. 10A and 10B. A mixture of three single stranded polynucleotides 45, 47 and 49 as shown in FIG. 10A are heat denatured and annealed to form a double stranded polynucleotide 51 which is an antiparallel nucleic acid double crossover molecule flanked by two four-arm branched junctions 57, 59. While the antiparallel nucleic acid double crossover molecule of FIG. 10A is shown to be formed by annealing three single stranded polynucleotides together based on their complementarity to each other and/or their self-complementarity, the same double crossover molecule can be formed from a number of different mixtures of single stranded polynucleotides. For instance, instead of the ends 53, 55 each being formed from two single stranded polynucleotides 45, 49, the ends 53, 55 may be present on a single strand to form the outer half of the two four-arm branch junctions 57, 59.

Three different antiparallel nucleic acid double crossover molecules 60, 62 and 64 having predetermined growth enzyme recognition sites A, A', B, B', etc., at predetermined locations (preferably at the ends of arms of double crossover molecules 60, 62, and 64) are cleaved at growth enzyme recognition sites L', L, Z' and Z, and then ligated to form a polynucleic acid structure 66 of three linked antiparallel nucleic acid double crossover molecules. Following assembly of the linked structure 66, cleavage at other growth enzyme recognition sites to expose cleaved ends and intramolecular ligations of pairs of complementary cleaved ends, i.e. N and N', M and M' etc., to arrive at the octahedron 68 can be performed in one or more series of restriction and ligation steps.

The three dimensional polynucleic acid structure 68 is shown in FIG. 10B as a Schlegel diagram representation of an octahedron. A Schlegel diagram representation of a three dimensional structure can be likened to a polar map of the world where the North Pole is at the center and is viewed as being closest to the viewer. The South Pole is then at every point on the circumference of the diagram and is dimensionally furthest from the viewer. Thus, the outer triangle is the back face of the octahedron furthest from the viewer. Both distance and distortions increase as points on the diagram move away from the center. There are only three antiparallel nucleic acid double crossover molecules, each being flanked by two four-arm branched junctions in this octahedron, whose growth enzyme recognition sites are represented as staggered and indicated by letters.

Two means of representing a three dimensional octahedron in two dimensions are illustrated in FIGS. 11A and 11B. Both the Schlegel diagram representation in FIG. 11A (equivalent to the Schlegel diagram in FIG. 10B) and the plan view representation in FIG. 11B indicate one of the three antiparallel nucleic acid double crossover molecules 60 with two flanking four-arm branched junctions bounded by staggered ends M-Y-X'-B-L'-A' in solid black. The octahedron of FIG. 11B viewed down one of its three-fold axes shows only four of its eight equilateral triangular faces containing three double crossover molecules whose free helical domains span a three-dimensional space. The three edges or linear arms constructed from DAE molecules are not coplanar, but span a three dimensional space. Thus, the linear arms 54 in FIGS. 11A and 11B will not intersect each other, no matter how far they are extended.

In the protocol for constructing the octahedron 68 of FIG. 10B, one of the three double crossover molecules 60, 62 or 64 can be attached to a solid support, e.g. at a growth enzyme recognition site on one helical domain such as indicated by reference numeral 70 in FIG. 10B, similar in manner to the protocol for assembling a truncated octahedron in Zhang et al., 1994, supra. Like the protocol described in Zhang et al., 1994, supra, intermolecular ligations of double crossover molecules 60, 62 and 64 in FIG. 10B preferably occur at sites distal to the growth enzyme recognition site (e.g. as with BbsI, BsmAI, Bbv I restriction enzymes, etc.) and intramolecular ligations in FIG. 10B preferably occur at pairs of different six-base symmetric recognition sites (e.g., BamHI and BglII) that expose complementary staggered ends with the result that the recognition sites are destroyed upon intramolecular closure of the structure by ligation. While the above described growth enzyme recognition sites, which are cleaved distal to the recognition site or which are destroyed upon ligation to a complementary staggered end, are preferred, other growth enzyme recognition sites can also be used to arrive at the desired three dimensional polyhedron structure. The protocol presented in FIGS. 10A and 10B and described in Zhang et al., 1994, supra, is a preferred, but non-limiting, embodiment of a method for constructing a three dimensional polyhedron. The octahedron structure 68 of FIG. 10B can be further extended into a three dimensional array of tetrahedrons by cleavage and subsequent ligation of complementary staggered ends from different tetrahedron molecules, which were generated at growth recognition sites located at the ends of helical domains 70, 71, 73. When each of the linear arms 54 are connected to a corresponding arm in another octahedron, the resulting structure then nucleates a structure resembling the arrangement of octahedral subunits in cubic close packed structures (face centered cubic structures), but of lower symmetry.

FIG. 12 illustrates a protocol for constructing a tetrahedron from two antiparallel nucleic acid double crossover molecules 72, 74 each flanked by two three-arm branched junctions. Two ends can be cleaved at growth enzyme recognition sites Y and Y' strand, which after intermolecular ligation forms structure 78. Further cleavage at growth enzyme recognition sites W, W', X, X', Z and Z' and subsequent intramolecular ligations leads to the tetrahedron structure 80 having two helical domains 82, 84 which, while appearing to be parallel to each other in a two dimensional representation, are actually perpendicular to each in the three dimensional structure. The ends of helical domains 82, 84 can be cleaved at a predetermined growth enzyme recognition site to generate staggered ends which are then connected to a corresponding end of another tetrahedron to construct extended arrays of tetrahedrons in two dimensions. Three dimensional arrays can be constructed if the separation between tetrahedrons as connected at helical domains 82, 84 are not integral multiples of double helical half turns.

Another embodiment of a polyhedron structure comprising antiparallel nucleic acid double crossover molecules is illustrated in FIG. 13. Six double crossover molecules 86 each having two flanking five-arm branched junctions are assembled in a sequential manner similar to the protocol described for a truncated octahedron (Zhang et al., 1994, supra) to produce an icosahedron 88, shown in FIG. 13 as a Schlegel diagram representation. This icosahedron structure 88 can also be further extended into a three dimensional array by connecting helical domains 90 having growth enzyme recognition sites at their ends.

FIG. 15 illustrates a third embodiment of a two dimensional lattice with an arrangement similar to FIG. 8 and exemplifies another means of utilizing double crossover molecules that contain an extra junction 48. However, the extra junction 48 is used to form the triangles, so that it is an integral part of the lattice itself, unlike the extra junction 30 of FIG. 9. Thus, one double crossover molecule is used to buttress the edge of another double crossover molecule and keep its helix axis linear.

FIG. 14A illustrates the construction of the buttressed triangles 92. Three antiparallel nucleic acid double crossover molecules 91, 93, 95 each having a first 94, second 96, and third 98 helical domains are cleaved at growth enzyme recognition sites and ligated together to form the buttressed triangle 92. The helix axes of the first 94 and second 96 domains are parallel to one another, whereas the helix axes of the third 98 domain emanates from between crossover sites 97, 99 in the middle of the second 96 domain at a bulged junction 100. The bulge at junction 100 has the advantage of overcoming possible steric constraints caused by the tightness of the junction between the second and third domains and the angle between the second and third helical domains is chosen to link one end, e.g., 101 of a second domain of one double crossover molecule with one end of the third helical domain, e.g. 103, of another double crossover molecule. Thus, in forming the nucleic acid triangle 92 according to FIG. 14A, the second domain of one double crossover molecule is connected to the third domain of an adjacent double crossover molecule at complementary staggered ends to buttress the edges of nucleic triangle 92 and keep the helix axis of each second domain linear.

In FIG. 15, each buttressed triangle 92 is connected to an adjacent buttressed triangle by joining corresponding ends of the second helical domain 96 (shown in FIG. 14A). Alternatively, two buttressed triangles 104 can be connected to each other by their corresponding first helical domain 106 (FIG. 14B). Furthermore, FIG. 14C illustrates two buttressed triangles 104 that connect an end of their first helical domain 106 to an end of the second helical domain 108 of the adjacent buttressed triangle. Thus, the buttressed triangles 104 of FIG. 14C result in a linear series of four crossovers along the two parallel helix axes that form the connection between adjacent buttressed triangles. An extended array of buttressed triangles according to FIG. 14C is expected to provide a highly rigid polynucleic acid structure.

Although the rigid topologically closed nucleic acid motifs and symmetrical structures formed from such motifs exemplified in the drawings use DAE molecules, the same types of rigid motifs and structures can be constructed from DAO molecules. In the case of a nucleic acid triangle constructed of DAO molecules, the protocol diagrammed in FIG. 6 would only need to be modified to mix two individual strands 1', 2' (see FIG. 2B) together and then anneal and ligate to form a triangle. As DAO molecules appear to be better behaved than DAE molecules, it is likely that the complex symmetrical structures formed from motifs composed of DAO molecules are at least as effective as those having DAE molecules. Moreover, the polynucleic acid structures of the present invention can be a mixture of DAE and DAO molecules which could fit into segments of the same length as edges of triangles by using a longer outside connecting segment.

Persons of ordinary skill in the art will appreciate that, in the method of constructing two dimensional and three dimensional polynucleic acid structures, the step of ligating together cleaved ends of nucleic acid molecules having a rigid motif may be repeated any number of times, and can also be alternated with further additions of monomeric rigid nucleic acid motifs to expand the periodic lattice (and thereby its size). In addition, it may be advantageous to bind one or more of the rigid nucleic acid motifs serving as building block components to a solid phase so as to facilitate the separation and purification of the two dimensional or three dimensional polynucleic acid structures from all unwanted reagents, by-products, etc., by simple washing. Any means of linking a polynucleotide to a solid phase may be used, but for more efficient production, the linkage should be easily cleavable under conditions which do not harm the structure.

It may be further advantageous to provide a solid phase material to bind a selected number of rigid nucleic acid motifs, such as triangles and polyhedrons, in a predetermined pattern of having a predetermined spacing in order to establish a boundary or perimeter, etc., the inside of which can be filled in with the developing lattice constructed from units of rigid nucleic acid motifs.

It may also be preferable to remove any small oligonucleotide molecules produced as a result of cleavage with growth enzymes in the method of producing a two dimensional or three dimensional nucleic acid structure. A variety of well-known methods such as alcohol precipitation, microfiltration, etc., may be employed to eliminate these undesirable oligonucleotides. Likewise, they can be synthesized with biotin groups and removed by treatment with streptavidin beads (Qi et al., 1996, supra).

While the growth enzymes, such as restriction enzymes, were designed for cleaving DNA, other enzymes may also be used for cleaving other polynucleotides. For example, RNA splicing enzymes and even non-enzyme chemicals which cleave the polynucleotide at a relatively specific site, may be considered "growth enzymes" for the purpose of the present invention.

One advantage for forming a closed, topologically-bonded molecule, i.e. triangle, polyhedron, as the basic unit to assemble a two dimensional or three dimensional nucleic acid structure is that, after successful ligation takes place, this allows the product to be subjected to vigorous treatment (e.g., heat denaturation or phenol extraction to remove enzymes), without irreversibly disrupting the structure. The unique closed-covalent nature of the successfully ligated product means that product failures will be susceptible to treatment with an exonuclease (e.g., exonuclease III) or other similar means to destroy unsuccessfully ligated molecules. Because the successful ligation results in a topologically closed molecule, exonuclease III treatment only destroys the failure products, not the successful ligation.

It should be appreciated that the term "nucleic acid" refers to both DNA and RNA and hybrids of the two. The structure need not resemble anything which can theoretically be made from nature.

A particular oligonucleotide or polynucleotide strand may employ bases other than the standard five, adenine, cytosine, guanine, thymine and uracil. Derivatized (e.g., methylated) and other unusual bases such as iso-guanine, iso-cytosine, amino-adenine, K, X, π, (Piccirilli et al. 343: 33–37, 1990), inosine and other derivatives of purine and pyrimidine may be used. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

Within a particular strand, the heterocyclic base may be entirely missing from the sugar moiety. This may be particularly desirable where the strands bend, form a junction, or where one desires fewer forces holding the strands together.

While the molecules employed in this invention generally have a double stranded region recognized by a restriction endonuclease, the molecules may have virtually anything attached to them. Note that biotinylated DNA has previously been used to assist in attaching a label to DNA used as a hybridization probe. The molecule employed may be quite large and only have a small "tail" of double stranded polynucleotide containing a growth enzyme site.

Linkers with plural ends ligatable to plural restriction sites may be employed to link diverse structures. Internal cyclizations are also likely to use a linker. While sticky (staggered) ends on both the structure and the linker are desirable, they are not required. Typically, linkers have at least one portion being a double stranded polynucleotide, but other different chemical moieties are acceptable.

A particular strand need not have a single contiguous ribose-phosphate or deoxyribose-phosphate backbone. One may employ a simple inorganic or organic moiety or polymeric spacer between segments of polynucleotide. Spacers such as polyethylene, polyvinyl polymers, polypropylene, polyethylene glycol, polystyrene, polypeptides (enzymes, antibodies, etc.) peptide nucleic acids (PNA), polysaccharides (starches, cellulose, etc.) silicones, silanes and copolymers, etc., may be employed. An example of such a hybrid structure is dodecadiol having phophoramidite at one end. This structure has been inserted covalently instead of four T nucleotides to form a hairpin loop in a fashion similar to the nucleotides it replaces. See Mitchel J. Doktycz, Ph.D. Thesis (1991), University of Illinois, Chicago. The term "oligonucleotide", "polynucleotide" and "nucleic acid" are intended to cover all of these structures.

In nature and the field of molecular biology, double stranded DNA generally occurs in the B form. However, for the purposes of this invention it may be desirable for DNA or other double stranded polynucleotide to exist in the A, C, D or Z form. Various bases, derivations and modifications may be used to stabilize the structure in the A, C, D or Z form as well.

Three dimensional polynucleic acid structures are particularly well suited for use as a scaffolding medium since they are stiff molecules unlikely to be perturbed markedly by tethering smaller non-interactive molecules to it. Another application for this structure is in the formation of polycatenated polymers.

The structure also makes a suitable material for immobilizing enzymes and other catalysts. By employing an open design for the structure, one or more enzymes may be bound to the structure and still permit free mobility of substrates and products to and from the enzyme. Instead of binding the enzyme directly to the structure, the structure may form a cage to entrap the enzyme(s). This technique has additional advantages of not modifying the enzyme.

Conventional enzyme immobilization techniques depend on random attachment and thus the solid phase particles formed are not uniform in either activity or structure. By contrast, one can attach a predetermined number of enzymes to the polynucleotide strands being added to form a structure with a fixed number and orientation of enzymes.

The structure may be so formed to create a mesh or screen-like material. This material can be used as a filter of very precise porosity. For added strength, plural layers of mesh may be linked together or a layer may be bound to any other conventional substrate.

The structures of and produced by the present invention have numerous two dimensional and three dimensional structural uses. Because of the minute size of the structures, they have application in the developing field of nanotechnology. A polyhedron alone or with internal supporting structures may act as a very small ball bearing and be used as a lubricant. Larger structures may be abrasives.

More current uses include use as a solubilizer or stabilizer for chemicals, particularly pharmaceuticals. For example, a drug may be bound to the interior of a three dimensional polynucleic acid structure. Since DNA degrades in acidic conditions and RNA degrades in alkaline conditions, one can direct the drug to be released in whatever part of the digestive system desired.

Furthermore, the interior of the structure may be made so as to carry hydrophobic chemicals or drugs to be solubilized in aqueous solutions. An analogous technique has been applied previously with steroids and hydroxyl propyl β-cyclodextrin with success. The reverse situation may also be performed in organic solutions, such as by removing the bulk of the charges on the nucleic acids, e.g., by substituting the bulk of methyl phosphonates for phosphates.

Another expected use is to design a specific binding structure. Since the distances and changes may be controlled at will, one can construct a receptor for a chemical. This may act as an adsorbent for separation or purification. Alternatively, the structure may be labeled and used as a specific binding reagent as is conventionally used in the field of analytical chemistry. If the structure is designed to bind an unstable intermediate, it may act as a catalyst as has been done with monoclonal antibodies.

Having now described the invention, the same will be more readily understood through reference to the following example which is provided by way of illustration and is not intended to be limiting of the present invention.

EXAMPLE 1

Ligation involving an antiparallel molecule with an even number of half turns is amenable to simple analysis because one strand can be isolated as a molecule that reports both linear and cyclic products and is presented in this example. The products of ligating the molecule with an odd number of half-turns between crossover points are much more complex, and do not include a simple reporter molecule. Surprisingly, DAE double crossover molecules were discovered to be capable of being ligated extensively without showing a large propensity to cyclize. This is shown for two sub-classes of DAE molecules: (1) molecules in which the cyclic strand between junctions is a simple unclosed loop; and (2) molecules in which the cyclic strand between junctions participates in a 3-arm bulged junction. Both classes of molecules are stiffer than branched junctions with the same sequence and the simple double crossover is at least as stiff as linear duplex DNA of the same sequence as determined in the ligation assays.

MATERIAL AND METHODS

The following general procedures were used in the present example:

Strand and Sequence Design

DAE molecules closely related to those characterized previously in Fu, T. J., and Seeman, N. C., *Biochem.* 32: 3211–3220, 1993, are used. There is little question about the preferred crossover isomers in the DAE (DAO) system, but sequences for flanking the junctions were chosen that correspond to those in the well-characterized branched junction, J1 (Churchill et al., *Proc. Nat. Acad. Sci.* (*USA*) 85: 4653–4656, 1988). The second domain $dT_4$ loops that terminate arms containing 5-nucleotide pairs were closed. This procedure permits the user to minimize the number of strands that must be titrated together, and it also ensures the integrity of the product. Slight modifications have been made to the initially designed sequence in the course of the work.

Synthesis and Purification of DNA

DNA molecules were synthesized on an Applied Biosystems 380B automatic DNA synthesizer, then removed from the support, and deprotected using routine phosphoramidite procedures (Caruthers, M. H., *Science* 230: 281–285, 1985). All strands were purified by polyacrylamide gel electrophoresis.

Formation of Hydrogen-bonded Complexes

Complexes were formed by mixing a stoichiometric quantity of each strand, as estimated by $OD_{260}$. This mixture was then heated to 90° C. for 5 minutes and cooled to the desired temperature by the following protocol: 20 minutes at 65° C., 20 minutes at 45° C., 30 minutes at 37° C., 30 minutes at room temperature, and (if desired), 30 minutes at 4° C. Exact stoichiometry was determined, if necessary, by titrating pairs of strands designed to hydrogen bond together, and visualizing them by native gel electrophoresis; absence of monomer was taken to indicate the endpoint.

Hydroxyl Radical Analysis

Individual strands of the DAE complexes were radioactively labeled, and were additionally gel purified from a 10–20% denaturing polyacrylamide gel. Each of the labeled strands (approximately 1 pmol in 50 mM Tris-HCL (pH 7.5) containing 10 mM $MgCl_2$ was either (1) annealed to a ten-fold excess of the unlabeled complementary strands; (2) annealed to a ten-fold excess of a mixture of the other strands forming the complex; (3) left untreated as a control; or (4) treated with sequencing reagents for a sizing ladder (Maxam et al., *Proc. Natl. Acad. Sci* (*USA*) 74: 560–564, 1977). The samples were annealed by heating to 90° C. for 3 min. and then cooled slowly to 4° C. Hydroxyl radical cleavage of the double-strand and double-crossover-complex samples for all strands takes place at 4° C. for 2 min and 40 seconds (Tullius, et al., *Science* 230: 679–681, 1985), with modifications noted by Churchill, et al (Churchill et al., *Proc. Natl. Acad. Sci.* (*USA*) 85: 4653–4656, 1988. The reaction was stopped by addition of thiourea. The sample was dried, dissolved in a formamide/dye mixture, and loaded directly onto a 10–20% polyacrylamide/8.3M urea sequencing gel. Autoradiograms were analyzed on a BioRad GS-250 Molecular Imager.

Polyacrylamide Gel Electrophoresis

Denaturing Gels

These gels contain 8.3 M urea and were run at 55° C. Gels contain 10% acrylamide (19:1, acrylamide:bisacrylamide). The running buffer is 89 mM Tris-HCl, pH 8.0, 89 mM boric acid, 2 mM EDTA (TBE). The sample buffer is 10 mM EDTA, containing 0.1% Xylene Cyanol FF tracking dye. Gels were run on an IBI Model STS 45 electrophoresis unit at 70 watts (50 v/cm), constant power, or on a Hoefer SE 600 electrophoresis unit at 60° C. (28 v/cm, constant voltage). They were then dried onto Whatman 3 MM paper and exposed to X-ray film for up to 15 hours.

Non-denaturing Gels

Gels contain 8–20% acrylamide (19:1, acrylamide:bisacrylamide). DNA were suspended in 10–25 μL of a solution containing 40 mM Tris-HCl, pH 8.0, 20 mM acetic acid, 2 mM EDTA and 12.5 mM magnesium acetate (TAEMg); the quantities loaded vary as noted below. The solution was boiled and allowed to cool slowly to 16° C. Samples were then brought to a final volume of 10 μL with a solution containing TAEMg, 50% glycerol and 0.02% each of Bromophenol Blue and Xylene Cyanol FF tracking dyes. Gels were run on a Hoefer SE-600 gel electrophoresis unit at 11 volts/cm at 16° C., and exposed to X-ray film for up to 15 hrs or stained with Stainsall dye.

Enzymatic Reactions

A. Kinase Labeling 10 pmols of an individual strand of DNA are dissolved in 20 μL of a solution containing 66 mM Tris-HCl, pH 7.6, 6.6 mM $MgCl_2$, 10 mM dithiothreitol (DTT), and mixed with 2 μL of 2.2 μM $\gamma$-$^{32}$P-ATP (10mCi/ml) and 6 units of polynucleotide kinase (Boehringer Mannheim, Indianapolis, Ind.) for 2 hrs at 37° C. Radioactive labeling was followed by addition of 1 μl of 10 mM unlabeled ATP, with incubation proceeding for another 10 min. The reaction was stopped by heat inactivation, followed by gel purification.

B. Ligations

Ligations were performed in the kinase buffer, which was brought to 66 μM ATP. 10 units of T4 polynucleotide ligase (U.S. Biochemical, Cleveland, Ohio) were added, and the ligation allowed to proceed at 16° C. for 10–16 hours. The reaction was stopped by phenol/chloroform extraction. Samples to be restricted were ethanol precipitated.

C. Restriction Endonuclease Digestions

Restriction enzymes are purchased from New England Biolabs, Beverly, Mass., and used in buffers suggested by the supplier. Digestion was performed at 37° C. for 2 hrs with 20 units of Hha I or 10 of Rsa I. The reaction was stopped by two or three phenol extractions.

D. Exonuclease III Treatment 100 units of exonuclease III (exo III), purchased from U.S. Biochemical, Cleveland, Ohio, was added directly to the ligation mixture, and the reaction was allowed to proceed for 0.5–2 hrs at 37° C. The reaction was stopped by heat inactivation.

E. Exonuclease I Treatment 100 units of exonuclease I (exo I), purchased from U.S. Biochemical, was added directly to the ligation mixture, and the reaction was allowed to proceed for 0.5–2 hrs at 37° C. and then stopped by heat inactivation.

RESULTS

Assembly of the Molecules.

Previously, the laboratory of the present inventors has shown that it is possible to assemble DAE-type double crossover molecules by hybridizing their constituent strands. Nevertheless, DAE molecules containing two closed ends have never before been reported. FIGS. 16A and 16B illustrate a non-denaturing gel containing the constituents of the DAE molecule being studied here. In some lanes, there have been two modifications to the sequence here, relative to the one whose sequence is shown in FIG. 17B (which is the same as that of FIG. 3A): (1) the d(AC) sequence shown at the 3' end of strand 2 is a d(TG), and residues 5 and 6 of strand 3 have been changed to d(CA); and (2) the sequence of strand 2 has (for most lanes) been permuted cyclically (strand 2a in FIG. 3B), so that the sequenced (CGGC) is at the 3' end of the strand, thereby eliminating the sticky end. The sequence was modified from the sequence used for this gel, because ligation experiments revealed that ligase sometimes inserted strand 1a (FIG. 17B) at the 5' end of the product in place of strand 2. The cyclic permutation of strand 2 was done to eliminate association of the cohesive ends on the gel that obscured the information sought. The version used in the present example contains the nick in the central strand permuted to be across from strand 3.

Lanes 1, 2, 3 and 4 contain the single strands that make up the various components of the complexes used. The multimerization of strand 1 (the 42-mer that forms the junction from strand 1) in lane 1 provides convenient molecular weight markers. Strand 1a, in lane 2, is designed just to produce the DAE molecule, without the extra crossover. Lane 5 contains the complete double crossover with the extra junction, formed using strand 1. Lane 6 contains the complete double crossover formed using strand 1a. Lane 7 contains the same molecule, but strand 3 (now composed of strands 3a and 3b) has been nicked across from the nick in permuted strand 1a, to create two bonded junctions, rather than a double crossover molecule. Lanes 9–11 contain the paired complexes with strand 1. Lane 8 illustrates the nature of the complex when the unpermuted version of strand 2 is used: Very little of the material has penetrated the gel, and that which has is smeared. Note that, in contrast, the material in lanes 5, 6 and 7 moves as a single discrete band, indicative of closed complexes, rather than open complexes (Wang et al., *Biochemistry* 34: 920–929, 1995). Relative to the markers in lane 1, these complexes migrate with mobilities similar to those expected for their molecular weights. Thus, they appear to be well-formed discrete complexes.

Hydroxyl Radical Autofootprinting Analysis

Hydroxyl radical autofootprinting has been used in the laboratory of the present inventors in the past to characterize a number of unusual DNA molecules, such as branched junctions (Wang et al., 1991, supra; Churchill et al., *Proc. Natl. Acad. Sci.* (*USA*) 85: 4653–4656, 1988; Chen et al., *Biochemistry* 27: 6032–6038, 1988; Kimball et al., *J. Biol. Chem.* 265L 6544–6547, 1990), antijunctions and mesojunctions (Wang et al., 1995, supra; Du et al., *Biochemistry* 31: 10955–10963, 1992), in addition to previous work with double crossovers (Fu et al., 1993, supra; Zhang et al., 1993, supra; Zhang et al., 1994, supra). These experiments were performed by labeling a component strand of the complex and exposing it to hydroxyl radicals. The key feature noted in these experiments is decreased susceptibility to attack in the comparison between the pattern seen when the strand is part of the complex, relative to the pattern derived from duplex DNA. Decreased susceptibility is interpreted to suggest that access to the hydroxyl radical is limited by steric factors at the sites where it is detected. Likewise, similarity to the duplex pattern at points of potential flexure is assumed to indicate that the strand has adopted a helical structure in the complex, even though this is not required by the secondary structure. In previous studies of double crossovers, protection has been seen both at the crossover sites and at non-crossover sites where strands from the two domains appear to occlude each other's surfaces from access by hydroxyl radicals (Fu et al., 1993, supra; Zhang et al., 1993, supra; Zhang et al., 1994, supra)

The results of these experiments are shown in FIGS. 17A–B and 17A–B. Each panel contains one-dimensional traces of the gel containing the products of hydroxyl radical treatment, in which linear duplex (DS) is compared with the double crossover molecule (DC). The results are summarized in FIGS. 17B and 17B in schematic form: Filled triangles of large and small sizes indicate nucleotides in the double crossover molecule that show large and small protections (respectively) relative to the linear duplex baseline. In the simple DAE molecule (FIG. 17A), extensive protection is visible at the two nucleotides flanking the branch points and the one 5' to them, as noted previously (Fu et al., 1993, supra; Zhang et al., 1993, supra; Zhang et al., 1994, supra; Churchill et al., 1988, supra). A weak protection is seen on the non-crossover strands in the central part of the molecule, four nucleotides 3' to the crossover sites. These sites have also been noted previously, and appear to be due to occlusion of the two strands by each other. Analogous protection is also visible on strand 3 at a site four nucleotides 3' to the left junction. Weak protection is also noted on the third nucleotide of the two hairpins. This protection pattern is similar to patterns noted previously for DAE double crossover molecules (Fu et al., 1993, supra), suggesting that the molecule has adopted the conformation expected for it.

The pattern in the molecule containing the bulged junction is shown in FIGS. 18A and 18B. Protection is again visible in the nucleotides flanking the junctions on strands 1 and 3, but the protection is somewhat weaker here, in comparison with the pattern seen for the molecule without the bulged junction. In addition, protection is seen 5' and 3' to the bulged junction on strand 1, as well as 5' to it on strand 2.

The present inventors are unaware of previous hydroxyl radical analysis of a bulged junction generated by free Fe(II)EDTA$^{2-}$. However, Zhong, et al., *Biochemistry* 33: 3660–3667 (1994), have analyzed an analogous molecule with other chemical probes, including hydroxyl radicals that were generated by MPE-Fe(II)EDTA$^{2-}$. The expectation is that the two domains of this junction containing strand 2 should stack upon each other, with the third domain being somewhat perpendicular to it (Leontis et al., 1991, supra; Leontis et al., *J. Biomol. Str. & Dyns.* 11: 215–223, 1993). The protections seen on the two sections of strand 1 that are nominally bent are in agreement with this model and with previous hydroxyl radical experiments on conventional 3-arm junctions (Du et al., 1992, supra; Guo et al., *Biochemistry* 29: 10927–10934, 1990), in which one strand is virtually unprotected, and the other two are more strongly protected. The protection on strand 2 is ascribed to its occlusion by strand 3, as in the molecule lacking the bulged junction. These data are consistent with a model in which one strand of the bulged junction is not very different from helical, and two strands contain bends. Thus, the hydroxyl radical patterns of both molecules are consistent with a reporter strand (strand 2) that does not differ significantly from a helical conformation. The partial structural characterization by hydroxyl radical analysis contains no indications that the molecules are behaving in an unexpected fashion.

Ligation Experiments

The two DAE molecules were ligated, one without a branched junction in the central section, and a second containing a branched junction in that region. FIGS. 19A and 19B show a denaturing gel that contains the results of the ligation experiments in the molecules lacking the extra junction. Lane 1 contains the products of ligating a standard marker that produces a ladder of both linear and cyclic single strands (Mueller et al., *J. Am. Chem. Soc.* 350: 6306–6308, 1991). Lane 2 contains the products of digesting the material in lane one with a mixture of exo I and exo III (termed exo I–III), to leave nothing but cyclic molecules. Lanes 3–8 all contain an equal amount of the cyclic single-stranded 42-mer, so as to permit calibration of the densities in each lane. Lanes 3 and 5 contain the products of ligating the DAE molecule without the extra junction, and lane 4 contains the products that result when the material in lane 3 is digested with exo I–III. The ligation ladder seen in lane 3 extends much longer than ligation ladders seen previously, involving the ligation of branched junctions. It appears to show products representing as long as 1-mers or 18-mers of the fundamental repeat. Nevertheless, treatment with exo I–III shows that all of these products are linear, in the sense that they are not cyclic molecules. True cyclic molecules in this system are complex catenanes that cannot be detected until product molecules are treated with Hha I restriction endonuclease to cleave strands 1 and 3 (the GCGC site one nucleotide pair from the right crossover in FIG. 17B). Lane 6 contains the products of treating the material in lane 5 with Hha I, in addition to exo I–III. No new exonuclease resistant material is seen in this lane. Thus, no detectable cyclic material is seen for this ligation experiment. Lane 7 contains the products of ligating the same molecule, but modified so that strand 3 is composed of two parts, strands 3a and 3b, and the nick on strand 1 has been rephased by 10 nucleotides to be opposite the gap between them. Thus, the molecule ligated here is effectively two branched junctions, rather than a single DAE molecule. Exo I–III treatment of the material in lane 7 reveals the ladder of cyclic products in lane 8. The cyclic molecules begin with the dimer (60 nucleotides) and proceed at least to the heptamer. This marker lane also shows that large cyclic molecules would not be detected in the body of the gel, but only in the region near the well.

FIGS. 20A and 20B illustrate a parallel and identical series of experiments, but now on the molecule containing a bulged, branched junction in the central region of the molecule. Inspection of lane 4 now shows a small amount of closed cyclic product, beginning with the dimer. The material noted in this lane is necessarily an artifact; until treatment with Hha I, single-stranded circles should not be seen in ligations where both strands are sealed. Lane 6 shows a trace of cyclization for this material, beginning with the dimer. The nicked junction experiment from FIG. 4a is repeated as a marker control in lanes 7 and 8.

Stiffness of the Molecules

It was discovered that DAE-type DNA double crossover molecules are very stiff in the ligation assay. It is possible to estimate the persistence length of DNA molecules from ligation assays (Livshits et al., *Biophys. J.* 68: A340–A340, 1995), if one has closed cyclic products in sufficient yield that it is possible to calculate j values (Kahn et al., *Nature* (London) 368: 163–166, 1994) (the ratio of cyclic to linear products) for a series of the ligation products.

Shore et al., *J. Mol. Biol.,* 170: 957–981, (1983) reported than an incommensurate twist can decrease the probability of cyclization markedly. The doubly-nicked DAE molecule only represents a partial control in this regard, because the two junctions it contains might well have twisting flexibility that compensates for an incommensurate twist. Our laboratory has shown that the twisting flexibility of branched junctions is less than the bending flexibility, but it still appears greater than in linear duplex DNA (Petrillo et al., 1988, supra). In order to see whether the 30-mer sequence that are polymerized are capable of cyclizing at all, a control ligation experiment was performed (Shore et al., *Proc. Natl. Acad. Sci.* (*USA*) 78: 4833–4837, 1981) on just that double helical sequence. The results of that experiment are shown in FIGS. 21 and 22.

FIG. 21 is a two-dimensional denaturing gel, in which the products of the ligation reaction were electrophoresed first in 6% acrylamide, and then in 10% acrylamide in a direction perpendicular to the first electrophoresis. In this type of gel, linear material runs on the diagonal, single-stranded circles run in an arc above the diagonal, and duplex circles in a second arc somewhat above the first (Ford et al., *Proc. Natl. Acad. Sci.* (*USA*) 91: 3117–3121, 1994). The duplex circles were sized by boiling them for about 10 minutes, so that some of them break to yield linear molecules and single circles, whose sizes can be compared with markers, as shown in FIG. 22. Not only is a readily detectable amount of duplex 150-mer circle seen, as expected, a trace of a 120-mer duplex circle is even made. Thus, unless the duplex is more flexible than the DAE molecule in the twisting direction, an artifact due to incommensurate twisting is not what is being observed.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A polynucleic acid structure, comprising at least one triangular unit having three edges, wherein at least one edge of said at least one triangular unit comprises an antiparallel nucleic acid double crossover molecule having two domains with parallel helical axes in which one domain of said antiparallel nucleic acid double crossover molecule forms an edge of said triangular unit and the second domain is extendible to connect to a corresponding second domain of an antiparallel nucleic acid double crossover molecule of an edge of another triangular unit.

2. A polynucleic acid structure in accordance with claim 1, wherein said at least one triangular unit is topologically closed.

3. A polynucleic acid structure in accordance with claim 1, wherein the polynucleic acid structure is planar.

4. A polynucleic acid structure in accordance with claim 1, wherein the polynucleic acid structure is three dimensional.

5. A polynucleic acid structure in accordance with claim 4, wherein the polynucleic acid structure is a delta-hedron.

6. A polynucleic acid structure in accordance with claim 4, wherein the polynucleic acid structure is an array of linked deltahedrons.

7. A polynucleic acid structure in accordance with claim 3, wherein the polynucleic acid structure comprises at least six triangular units, said triangular units being arranged with hexagonal symmetry.

8. A polynucleic acid structure in accordance with claim 1, wherein two of said three edges of said at least one triangular unit comprises an antiparallel nucleic acid double crossover molecule.

9. A polynucleic acid structure in accordance with claim 1, wherein each of said three edges of said at least one triangular unit comprises an antiparallel nucleic acid double crossover molecule having a first and a second domain with parallel helical axes, said first domain being connected to said second domain at two crossover sites.

10. A polynucleic acid structure in accordance with claim 9, wherein said antiparallel nucleic acid double crossover molecule of at least one edge of said at least one triangular unit further comprises a third helical domain connected at one end to said second domain between said two crossover sites and extendible to connect to a corresponding third domain of an antiparallel nucleic double crossover molecule of an edge of another triangular unit.

11. A polynucleic acid structure, comprising at least one triangular unit having three edges formed by three antiparallel nucleic acid double crossover molecules, each of said three antiparallel nucleic acid double crossover molecules having two crossover sites and a first, second, and third helical domains, each of said first, second, and third helical domains having a first and second end, said first and second helical domains having helical axes in parallel and being connected to each other at said two crossover sites, said first end of said third helical domain forming a junction with said second helical domain, said junction being disposed between said two crossover sites, said first end of said second helical domain of each antiparallel nucleic acid double crossover molecule being connected to said second end of said third helical domain of another antiparallel nucleic acid double crossover molecule to form an edge of a triangular unit.

12. A polynucleic acid structure in accordance with claim 11, wherein said second end of said second helical domain of each antiparallel nucleic acid double crossover molecule of a triangular unit being extendible to connect to a corresponding second end of a second domain of an antiparallel nucleic acid double crossover molecule of another triangular unit.

13. A polynucleic acid structure in accordance with claim 11, wherein said first end of said first helical domain of each antiparallel nucleic acid double crossover molecule of a triangular unit being extendible to connect to a corresponding first end of a first domain of an antiparallel nucleic acid double crossover molecule of another triangular unit.

14. A polynucleic acid structure in accordance with claim 11, wherein said first end of said first helical domain of each antiparallel nucleic acid double crossover molecule of a triangular unit being extendible to connect to said second end of said second helical domain of an antiparallel nucleic acid double crossover molecule of another triangular unit.

15. A polynucleic acid structure in accordance with claim 11, wherein said junction formed by said first end of said third helical domain and said second helical domain is a bulged junction.

16. A polynucleic acid structure in accordance with claim 11, wherein the polynucleic acid structure is planar.

17. A polynucleic acid structure in accordance with claim 11, wherein the polynucleic acid structure comprises at least six triangular units, said triangular units being arranged with hexagonal symmetry.

18. A method for producing the polynucleic acid structure of claim 11, comprising the steps of:

a) synthesizing at least two single stranded polynucleotides, each being self-complementary and/or complementary to another single stranded polynucleotide and capable of hybridizing to form at least one antiparallel nucleic acid double crossover molecules;

b) mixing the single stranded polynucleotides to form a mixture and heat denaturing the mixture;

c) annealing the mixture of at least two single stranded polynucleotides to form antiparallel nucleic acid double crossover molecules having a plurality of predetermined growth enzyme recognition sites at predetermined locations;

d) cleaving the antiparallel nucleic acid double crossover molecules at growth enzyme recognition sites with growth enzymes to generate staggered ends; and e) ligating complementary staggered ends of different antiparallel nucleic acid crossover molecules together to form a triangular unit.

19. The method in accordance with claim 18, further comprising, after step e), the steps of:

f) cleaving the triangular unit at a growth enzyme recognition site with a growth enzyme to generate staggered ends; and g) ligating complementary staggered ends of different triangular units together to form an array of linked triangular units.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:1:

```
GGAGCGGACG TTGCACACCT ATGCGCACCC TGCGTCCGCT CC                              42
```

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:2:

```
CGGCTGATCT CCTGTGCCAG GGACAACTTG                                            30
```

(2) INFORMATION FOR SEQ ID NO:3:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:3:

```
TGATCTCCTG TGCCAGGGAC AACTTGCGGC                                            30
```

(2) INFORMATION FOR SEQ ID NO:4:

(i) SEQUENCE CHARACTERISTICS:
      (A) LENGTH: 58 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:4:

```
GCCGCAAGTT GTGGAGCTTT TGCTCCTGCG CATAGGCAAT TTTTTAATTG GGAGATCA            58
```

(2) INFORMATION FOR SEQ ID NO:5:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:5:

```
                               -continued

CGGCTGATCT CCTGTGCCAG GGACAACTAC                                        30

(2) INFORMATION FOR SEQ ID NO:6:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:6:

GCCGGTAGTT GTGGAGCTTT TGCTCCTGCG CATAGGCAAT TTTTTAATTG GGAGATCA         58
```